(12) United States Patent
Dejardin

(10) Patent No.: US 11,534,210 B2
(45) Date of Patent: Dec. 27, 2022

(54) APPARATUS AND METHOD FOR MINIMALLY INVASIVE OSTEOSYNTHESIS OF SACROILIAC LUXATIONS/FRACTURES

(71) Applicant: BOARD OF TRUSTEES OF MICHIGAN STATE UNIVERSITY, East Lansing, MI (US)

(72) Inventor: Loic M. Dejardin, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 94 days.

(21) Appl. No.: 16/906,329

(22) Filed: Jun. 19, 2020

(65) Prior Publication Data

US 2020/0315669 A1 Oct. 8, 2020

Related U.S. Application Data

(62) Division of application No. 15/917,064, filed on Mar. 9, 2018, now Pat. No. 10,687,863.

(Continued)

(51) Int. Cl.
*A61B 17/17* (2006.01)
*A61B 17/88* (2006.01)
(Continued)

(52) U.S. Cl.
CPC ...... *A61B 17/7055* (2013.01); *A61B 17/1703* (2013.01); *A61B 17/1757* (2013.01);
(Continued)

(58) Field of Classification Search
CPC . A61B 17/34; A61B 17/3403; A61B 17/3421; A61B 17/3423; A61B 17/3445;
(Continued)

(56) References Cited

U.S. PATENT DOCUMENTS

| 4,558,857 A | * | 12/1985 | Heller | ............ A61G 13/02 5/608 |
| 6,689,142 B1 | * | 2/2004 | Tremaglio, Jr. | ... A61B 17/3496 604/114 |

(Continued)

OTHER PUBLICATIONS

Dejardin et al., Comparison of open reduction versus minimally invasive surgical approaches on screw position in canine sacroiliac lag-screw fixation, Vet. Comp. Orthop. Traumatol., 29:290-7 (2016).

(Continued)

*Primary Examiner* — Tessa M Matthews
(74) *Attorney, Agent, or Firm* — Marshall, Gerstein & Borun LLP

(57) ABSTRACT

The disclosure relates to a surgical system and related methods to facilitate reduction and fixation of sacro-iliac luxations/fractures (SIL/F) in small animals, for example dogs and cats. In another aspect, the disclosure relates to an aiming device and related methods providing accurate, reliable, and safe fixation of SIL/F in such small animals. The surgical system includes a work surface, an articulatable and lockable reduction arm mounted to the work surface, a reduction handle mounted to the reduction arm; an articulatable and lockable fixation arm mounted to the work surface, a fixation drill guide mounted to the fixation arm, and an image acquisition unit directed toward the work surface. The surgical system provides enhanced safety to surgical personnel using the system in terms of reduced exposure to harmful radiation form the image acquisition unit.

18 Claims, 11 Drawing Sheets

Related U.S. Application Data

(60) Provisional application No. 62/587,199, filed on Nov. 16, 2017, provisional application No. 62/469,652, filed on Mar. 10, 2017.

(51) Int. Cl.
| | | |
|---|---|---|
| *A61B 90/50* | (2016.01) | |
| *A61B 17/64* | (2006.01) | |
| *A61B 17/68* | (2006.01) | |
| *A61B 17/70* | (2006.01) | |
| *A61D 1/00* | (2006.01) | |
| *A61B 90/00* | (2016.01) | |
| *A61B 90/57* | (2016.01) | |

(52) U.S. Cl.
CPC ...... *A61B 17/7077* (2013.01); *A61B 17/8866* (2013.01); *A61B 90/50* (2016.02); *A61D 1/00* (2013.01); *A61B 17/6433* (2013.01); *A61B 90/39* (2016.02); *A61B 2017/681* (2013.01); *A61B 2090/571* (2016.02)

(58) Field of Classification Search
CPC . A61B 17/3468; A61B 17/3472; A61B 90/39; A61B 90/50; A61B 2017/681; A61B 17/1703–1792
See application file for complete search history.

(56) References Cited

U.S. PATENT DOCUMENTS

| | | | |
|---|---|---|---|
| 10,842,514 B2* | 11/2020 | Jain | A61B 90/50 |
| 2005/0065434 A1* | 3/2005 | Bavaro | A61L 29/18 |
| | | | 600/424 |
| 2006/0122495 A1 | 6/2006 | Kienzle | |
| 2013/0345718 A1 | 12/2013 | Crawford et al. | |
| 2014/0023475 A1* | 1/2014 | Meyers | B25J 1/00 |
| | | | 414/800 |
| 2014/0343572 A1 | 11/2014 | Windolf et al. | |
| 2014/0379038 A1 | 12/2014 | Dogramadzi et al. | |
| 2018/0049754 A1 | 2/2018 | Tarricone et al. | |
| 2018/0064497 A1 | 3/2018 | Hussain et al. | |
| 2018/0116758 A1* | 5/2018 | Schlosser | F16M 13/022 |
| 2018/0199951 A1 | 7/2018 | Chappuis et al. | |

OTHER PUBLICATIONS

Marturello et al., "Comparison of Open Reduction and Minimally Invasive Surgical Approaches on Screw Position in Canine Sacroiliac Lag-Screw Fixation," presented at European College of Veterinary Surgeons (EVCS) Annual Meeting (2015).

Fauron et al., "Minimally Invasive Sacroiliac Fixation Using a Dedicated Novel Instrument System," presented at Veterinary Orthopedic Society (VOS) Conference, Snowbird, Utah, Mar. 11-18, 2017.

Dejardin et al., Minimally invasive lag screw fixation of sacroiliac luxation/fracture using a dedicated novel instrument system: Apparatus and technique description, Veterinary Surgery, 2017:1-11 (2017).

\* cited by examiner (A)

(B)

(C)

APPARATUS AND METHOD FOR MINIMALLY INVASIVE OSTEOSYNTHESIS OF SACROILIAC LUXATIONS/FRACTURES

CROSS-REFERENCE TO RELATED APPLICATIONS

This application is a division of U.S. patent application Ser. No. 15/917,064 (filed Mar. 9, 2018), which claims the priority benefit of U.S. Provisional Application No. 62/469,652 filed Mar. 10, 2017 and to U.S. Provisional Application No. 62/587,199 filed Nov. 16, 2017, all of which are incorporated herein by reference in their entireties.

STATEMENT OF GOVERNMENT INTEREST

None.

BACKGROUND OF THE DISCLOSURE

Field of the Disclosure

In one aspect, the disclosure relates a surgical system and related methods to facilitate reduction and fixation of sacroiliac luxations/fractures (SIL/F) in small animals (e.g., dogs and cats). In another aspect, the disclosure relates to an aiming device and related methods providing accurate, reliable, and safe fixation of SIL/F in such small animals.

Background

Open Reduction and Internal Fixation (ORIF): The surgical repair of SIL/Fs is most often performed using an ilio-sacral screw and washer applied in a lag fashion. Current techniques in veterinary orthopedics include ORIF which requires invasive surgical approaches. Post-operative morbidity, as well as suboptimal fixation have been reported with ORIF. These complications are principally related to poor alignment of the screw pilot hole with the safe sacral body corridor. This corridor represents a relatively thin and long bone cylinder within the sacral body and is perpendicular to the sagittal plane. As an example the safe sacral corridor in a Labrador size dog is ~1 $cm^2$ in cross section and ~5 to 6 cm long. Deviations from this axis may lead to violation of 1) the intervertebral space between the last lumbar vertebra (L7) and first sacral vertebra (S1) or 2) the spinal canal and its most distal nerve roots (cauda equina) and 3) poor screw anchorage in the thin sacral wing, all of which may result in severe complications and high post-operative morbidity.

Minimally Invasive Osteosynthesis (MIO): Alternatively, to reduce post-operative complication rates and optimize fixation, MIO techniques have been devised and are considered standard of care in human orthopedics. These techniques, which are slowly gaining acceptance in veterinary orthopedics, rely on indirect (radiographic) rather than direct (surgical exposure) visualization of the sacral target. Possible limitations of MIO include 1) mandatory reliance on intra-operative fluoroscopic imaging, which results in insidious and deleterious exposure of the surgical team to ionizing radiations, 2) time consuming accurate positioning and orientation of a drill guide over the sacral body to guarantee proper screw fixation and orientation in a narrow safe sacral implantation corridor, and 3) difficulty in maintaining reduction during surgery.

Currently, minimally invasive manual reduction of the sacro-iliac joint in small animals is typically accomplished by manipulation of the ischial tuberosity and/or iliac wing using bone reduction forceps or a Steinman pin. The reduction tools are manually handheld by the surgeon while reduction adequacy is ascertained fluoroscopically. Reduction is maintained with a temporary K-wire blindly implanted through the ilium and into the sacrum prior to lag screw fixation. Repositioning of the K-wire is often necessary to ensure sufficient stability while avoiding neurovascular structures surrounding the sacrum. Additionally, accurate orientation of the lag screw pilot hole within a narrow safe implantation sacral corridor is essential to optimize screw purchase and preserve adjacent neurovascular structures. During that phase, the drill sleeve is manually maintained in position while its orientation is verified fluoroscopically prior to drilling. Although instruments (e.g., a needle holder) may be used to hold the drill guide from a distance, the surgeon remains in close proximity to both a C-arm x-ray emitter and the surgical subject. Thus, throughout both reduction and drilling, the surgeon(s) proximity to the X-ray source and patient significantly increases exposure to primary beam and back-scattered radiation.

Radiation exposure can be substantially reduced based on "As Low As Reasonably Achievable" (ALARA) principles to incorporate shielding, reduced exposure time, and increased distance from a radiation source. Nonetheless, using current MIO techniques for SIL/F, surgical personnel remain in close proximity to the radiation source until reliable fixation is obtained. Further, successful screw placement ultimately relies on the surgeon's ability to maintain this optimal orientation while drilling, and aiming errors are a source of inaccuracy during drilling and represent an additional and critical limitation of current MIO repairs of SIL/F.

Drill guides: Commercially available drill guides are radio-opaque steel devices consisting of cylindrical tube (sleeve) attached to a handle. With MIO, the guide is first used to locate the sacrum and is then manipulated until its hollow shaft appears as a perfect circle centered over the sacral body. Once properly located, the drill guide must be maintained in position while the screw pilot and lag holes are drilled in the target bone(s). Two major design limitations can be identified when using conventional drill guides. First, the view of small sacral corridor (target bone) is partially obscured due to the radio-opacity of the guide and handle. This increases the risk of malalignment of the screw within the sacral body which in turn may lead to unsafe screw orientation and/or poor screw purchase and fixation. Second the cylindrical shape of the drill guide generates a linear radiographic image unless the drill guide is perfectly perpendicular to the sagittal plan of the sacral body (or parallel to the X-ray beam). In the absence of identifying markers at the extremities of the drill guide, corrective alignment maneuvers may be challenging and time consuming due to the nearly symmetrical projection of the guide over the target. This in turn needlessly increases anesthesia time and personnel exposure to radiation.

SUMMARY

In an aspect, the disclosure relates to a surgical system comprising: a work surface; a reduction arm (fixedly) mounted to the work surface at a proximal region (or end) of the reduction arm, wherein the reduction arm is articulatable relative to the work surface, and the reduction arm is lockable in position relative to the work surface; a reduction handle mounted to the reduction arm at a distal region (or end) of the reduction arm, wherein the reduction handle is adapted to attach to a surgical subject; a fixation arm (fixedly) mounted to the work surface at a proximal region (or end) of the fixation arm, wherein the fixation arm is articulatable relative to the work surface, and the fixation arm is lockable in position relative to the work surface; a fixation drill guide mounted to the fixation arm at a distal region (or end) of the fixation arm, wherein the fixation drill guide is adapted to receive a fixation screw (e.g., or other fixation means) therethrough for insertion into the surgical subject (e.g., and corresponding drill bit for pin insertion); and an image acquisition unit directed toward the work surface (e.g., adapted/positioned to acquire an image of a surgical subject on the work surface), wherein the image acquisition unit is lockable in position relative to the work surface.

Various refinements and embodiments of the surgical system are possible.

In a refinement, the surgical system comprises at least two reduction arms and at least two reduction handles.

In a refinement, the reduction arm comprises at least two reduction arm elements rotatably mounted to each other; and the fixation arm comprises at least two fixation arm elements rotatably mounted to each other.

In a refinement, the reduction handle comprises: a reduction rod comprising an insertion pin at a distal end of the reduction rod; and a reduction tube adapted to receive the reduction rod therethrough. In a further refinement, the reduction tube comprises a radiolucent material. In a further refinement, the reduction handle further comprises: a reduction sleeve slidably mounted to an (external) distal end of the reduction tube, the reduction sleeve being formed from a flexible material and having a tapered distal tip with longitudinal slots permitting expansion of the tapered distal tip.

In a refinement, the fixation drill guide comprises a minimally invasive lucent aiming device and drill guide according to any of its variously disclosed embodiments.

In a refinement, the fixation arm comprises two longitudinally extending retaining members at the distal region of the fixation arm and spaced apart by a distance of at least 1 cm; and the fixation drill guide is mounted to the fixation arm between the two longitudinally extending retaining members.

In a refinement, the work surface is articulatable.

In a refinement, the image acquisition unit is an x-ray imaging unit. In a further refinement, the image acquisition unit comprises an emitter unit and an intensifier unit; the emitter unit is positioned above the work surface; and the intensifier unit is positioned below the work surface.

In another aspect, the disclosure relates to a method for minimally invasive osteosynthesis of sacroiliac luxations/fractures, the method comprising: placing a surgical subject on the work surface of the disclosed surgical system in any of its various embodiments or refinements; attaching the reduction handle to the surgical subject; positioning and orienting the surgical subject using the reduction arm and the reduction handle; visually confirming proper position and orientation of the surgical subject using the image acquisition unit; locking the reduction arm in place relative to the work surface; inserting the fixation drill guide into the surgical subject at a position for minimally invasive osteosynthesis of a sacroiliac luxation or fracture in the surgical subject; positioning and orienting the fixation drill guide using the fixation arm; visually confirming proper position and orientation of the fixation drill guide using the image acquisition unit; locking the fixation arm in place relative to the work surface; and inserting a fixation screw through the fixation drill guide and into the surgical subject.

Various refinements and embodiments of the surgical method are possible.

In a refinement, positioning and orienting the surgical subject using the reduction arm and the reduction handle comprises: adjusting at least one of a position and an orientation of the surgical subject using the reduction arm and the reduction handle; locking the reduction arm in place relative to the work surface; and visually interrogating current position and orientation of the surgical subject using the image acquisition unit.

In a refinement, inserting the fixation drill guide into the surgical subject comprises: locating an insertion point using the image acquisition unit and an externally positionable radiopaque location marker; and inserting the fixation drill guide into the surgical subject at the insertion point.

In a refinement, positioning and orienting the fixation drill guide using the fixation arm comprises: adjusting at least one of a position and an orientation of the fixation drill guide using the fixation arm; locking the fixation arm in place relative to the work surface; and visually interrogating current position and orientation of the fixation drill guide in the surgical subject using the image acquisition unit.

In a refinement, the fixation drill guide comprises a minimally invasive lucent aiming device and drill guide according to any of its variously disclosed embodiments; and visually confirming proper position and orientation of the fixation drill guide using the image acquisition unit comprises confirming that the proximal aiming guides are aligned on axis with the distal aiming guides of the fixation drill guide.

In another aspect, the disclosure relates to a minimally invasive lucent aiming device and drill guide comprising: a drill guide sleeve defining a longitudinal axis therethrough and adapted to receive a fixation screw therethrough for insertion into a surgical subject; at least two radially extending radiopaque proximal (or cis or near) aiming guides positioned at different angular positions and extending outwardly from a proximal (or cis or near) end of the drill guide sleeve; and at least two radially extending radiopaque distal (or trans or far) aiming guides positioned at different angular positions and extending outwardly from a distal (or trans or far) end of the drill guide sleeve; wherein the angular position for each proximal aiming guide is the same as the angular position for a corresponding distal aiming guide.

Various refinements and embodiments of the minimally invasive lucent aiming device and drill guide are possible.

In a refinement, the aiming device and drill guide further comprises a radiolucent body enclosing or attached to the proximal aiming guides and positioned at the proximal end of the drill guide sleeve.

In a refinement, each corresponding pair of proximal aiming guides and distal aiming guides have relative lengths and widths (or diameter) such that one aiming guide is longer and narrower than the corresponding opposing aiming guide in the pair. In a further refinement, the proximal aiming guide is longer and narrower than the corresponding distal aiming guide in the pair.

In a refinement, the proximal aiming guides have lengths a range from 0.5 cm to 5 cm; and the distal aiming guides have lengths a range from 0.5 mm to 5 mm.

In a refinement, the drill guide sleeve defines an open interior volume having a width in a range from 1 mm to 10 mm.

In a refinement, the drill guide sleeve has a length in a range from 1 cm to 10 cm.

In a refinement, the drill guide sleeve comprises a radiolucent material.

In a refinement, the aiming device and drill guide comprises: four radiopaque proximal aiming guides at angular positions (Θ) of 0°, 90°, 180°, and 270°; and four corresponding radiopaque distal aiming guides at corresponding angular positions (Θ) of 0°, 90°, 180°, and 270°.

In another aspect, the disclosure relates to a reduction handle according to the variously disclosed embodiments herein. In a particular aspect, the disclosure relates to a reduction handle comprising: a reduction rod comprising an insertion pin at a distal end of the reduction rod; and a reduction tube adapted to receive the reduction rod therethrough. In a refinement, the reduction tube comprises a radiolucent material. In a refinement, the reduction handle further comprises: a reduction sleeve slidably mounted to an (external) distal end of the reduction tube, the reduction sleeve being formed from a flexible material and having a tapered distal tip with longitudinal slots permitting expansion of the tapered distal tip. In a refinement, the reduction rod and the reduction tube can be in the form of a unitary body (e.g., a single piece structure, in contrast to two separate pieces for a reduction rod and a reduction tube, respectively).

In another aspect, the disclosure relates to a kit for a surgical system, the kit comprising: a reduction arm adapted to be (fixedly) mounted to a work surface at a proximal region (or end) of the reduction arm, wherein the reduction arm is articulatable relative to the work surface, and the reduction arm is lockable in position relative to the work surface; a reduction handle adapted to be mounted to the reduction arm at a distal region (or end) of the reduction arm, wherein the reduction handle is adapted to attach to a surgical subject; a fixation arm adapted to be (fixedly) mounted to a work surface at a proximal region (or end) of the fixation arm, wherein the fixation arm is articulatable relative to the work surface, and the fixation arm is lockable in position relative to the work surface; and a fixation drill guide adapted to be mounted to the fixation arm at a distal region (or end) of the fixation arm, wherein the fixation drill guide is adapted to receive a fixation screw (e.g., or other fixation means) therethrough for insertion into the surgical subject (e.g., and corresponding drill bit for pin insertion). The reduction arm, reduction handle, fixation arm, and fixation drill guide (which can be a minimally invasive radiolucent aiming device and drill guide) can be included in the kit in any of their variously disclosed embodiments and in any quantities (e.g., a single piece of a given component, or a plurality of a given component). The kit components can be assembled or installed on a work surface and in proximity to an image acquisition unit to provide a surgical system according to the disclosure.

BRIEF DESCRIPTION OF THE DRAWINGS

For a more complete understanding of the disclosure, reference should be made to the following detailed description and accompanying drawings wherein.

Figure 1:
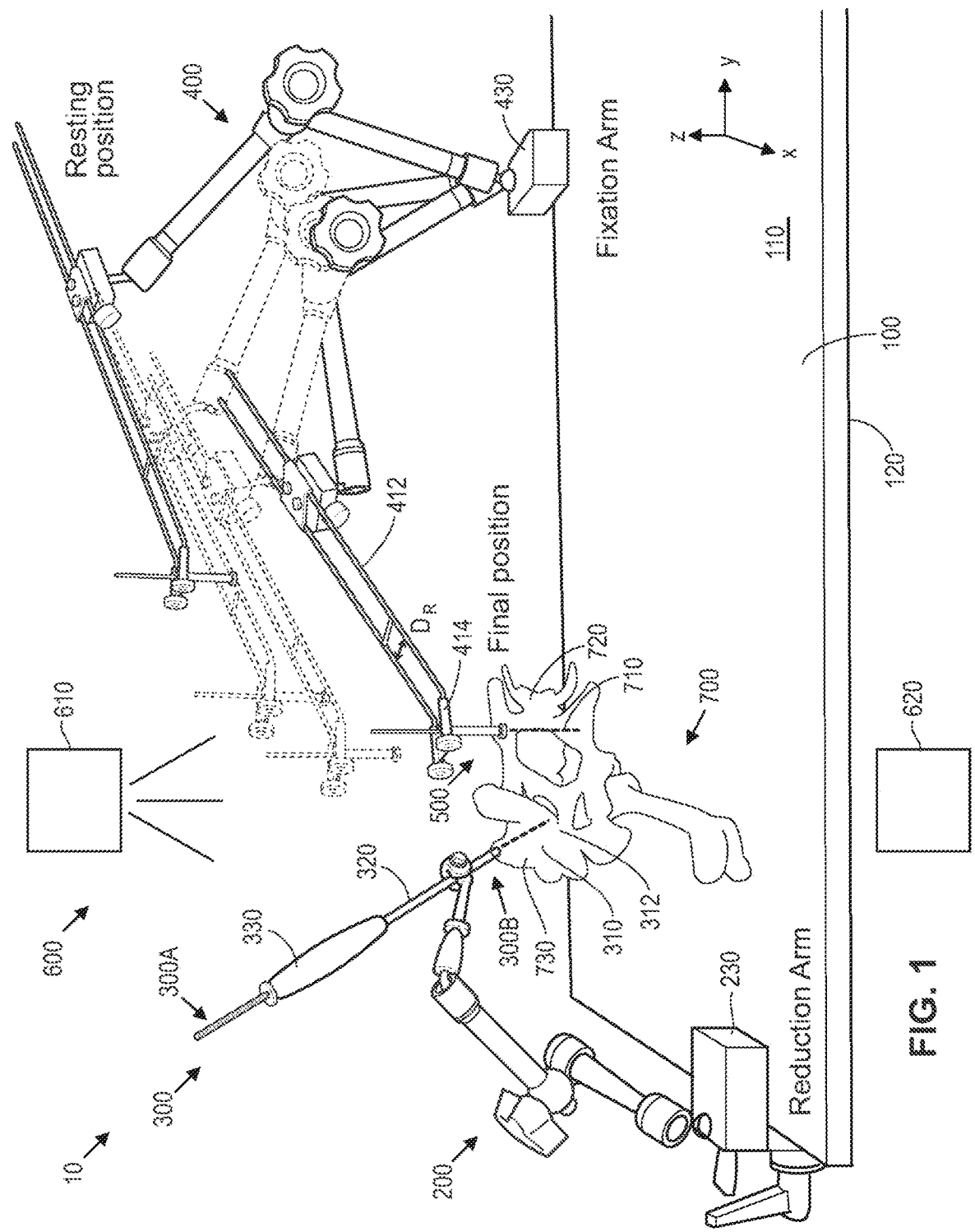
FIG. 1 illustrates a surgical system according to the disclosure, including a reduction handle, a fixation drill guide/aiming device, associated articulated arms for reduction and fixation, and a model of a skeletal section corresponding to a surgical subject.

While the disclosed apparatus, compounds, methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

DETAILED DESCRIPTION

In one aspect, the disclosure relates to a surgical system. To improve reduction and fixation of SIL/F while reducing radiation exposure, the disclosed surgical system includes a set of instruments dedicated to the minimally invasive surgical treatment of SIL/F, for example in dogs and cats. This instrumentation combines commercially available as well as custom designed equipment. Specific components may include but are not limited to articulated friction arms, universal joints, and quick couplers (e.g., available from Manfrotto, Italy); hexapods with 6-axis/degrees of freedom platforms and dedicated software (e.g., available from Newport Corp., CA; Physik Instrumente (PI) GmbH, Germany; Symetrie, France); drill guides, drill sleeves and associated drill bits (e.g., available from DePuy-Synthes, PA); and reduction handles and clamps (e.g., available from DePuy-Synthes, PA). A hexapod (6-axis/degrees of freedom platform) allows for displacement of a payload in 6 dimensions (i.e., 3 planes and 3 axes). These movements are described as: roll (e.g., rotation of the dorsal plane in the surgical case), pitch (e.g., rotation of the transverse plane in the surgical case), yaw (e.g., rotation of the sagittal plane in our case), heave (e.g., elevation off/toward the surgical table), surge (e.g., forward/backward motion), and sway (dorsal/ventral motion). In an embodiment, a platform in which motion would be limited to 3 degrees of freedom (e.g., roll/pitch/yaw only) can be used in place of 6-axis/degrees of freedom. The absence of the heave/surge/sway capability could be compensated by the articulated arms.

Articulated arms (e.g., fixation and/or reduction arms) can be either affixed to the surgical table directly or via hexapods. One arm (e.g., fixation arm) can be linked or attached to a set of drill guides and sleeves via suitable mounting fixtures. This arm can be used for SIL/F fixation. A second arm (e.g., reduction arm) can be similarly rigidly attached to the surgical table and can be used to maintain SIL/F reduction once achieved using the reduction handle(s). The handle(s) can be coupled to the reduction arm via suitable mounting fixtures. Reduction of the SIL/F as well as positioning of the drill guide over the sacral body can be performed using the articulated arms first for coarse positioning. In an embodiment, fine adjustments can be remotely controlled by actuating the hexapods while proper position of the instrumentation over the sacral body can be ascertained under fluoroscopic guidance. In another embodiment, fine adjustments can be achieved by manually actuating the hexapods while proper position of the instrumentation over the sacral body can be ascertained under fluoroscopic guidance.

In an aspect, the disclosure relates to a minimally invasive lucent aiming device and drill guide according which can be used with the disclosed system. The aiming device provides timely, accurate, reliable and safe targeting of the sacral body. The purpose of the aiming device is to optimize screw position over the sacral body as well as screw orientation within a safe sacral corridor, while minimizing soft tissue dissection, reducing radiation exposure as well as operating time. In an illustrative embodiment, the aiming device includes a radiolucent acrylic disk or body with four metal wires as proximal aiming guides, central sleeve manufactured from radiopaque or radiolucent materials (e.g., a hollow, tubular body serving as a drill guide), and a metal sleeve with four fins as distal aiming guides. The radiolucent disk or body of the aiming device can be secured to a circular tubular clamp as part of a rail-like sliding handle, which can be attached to the fixation arm in the corresponding surgical system.

Figure 2:
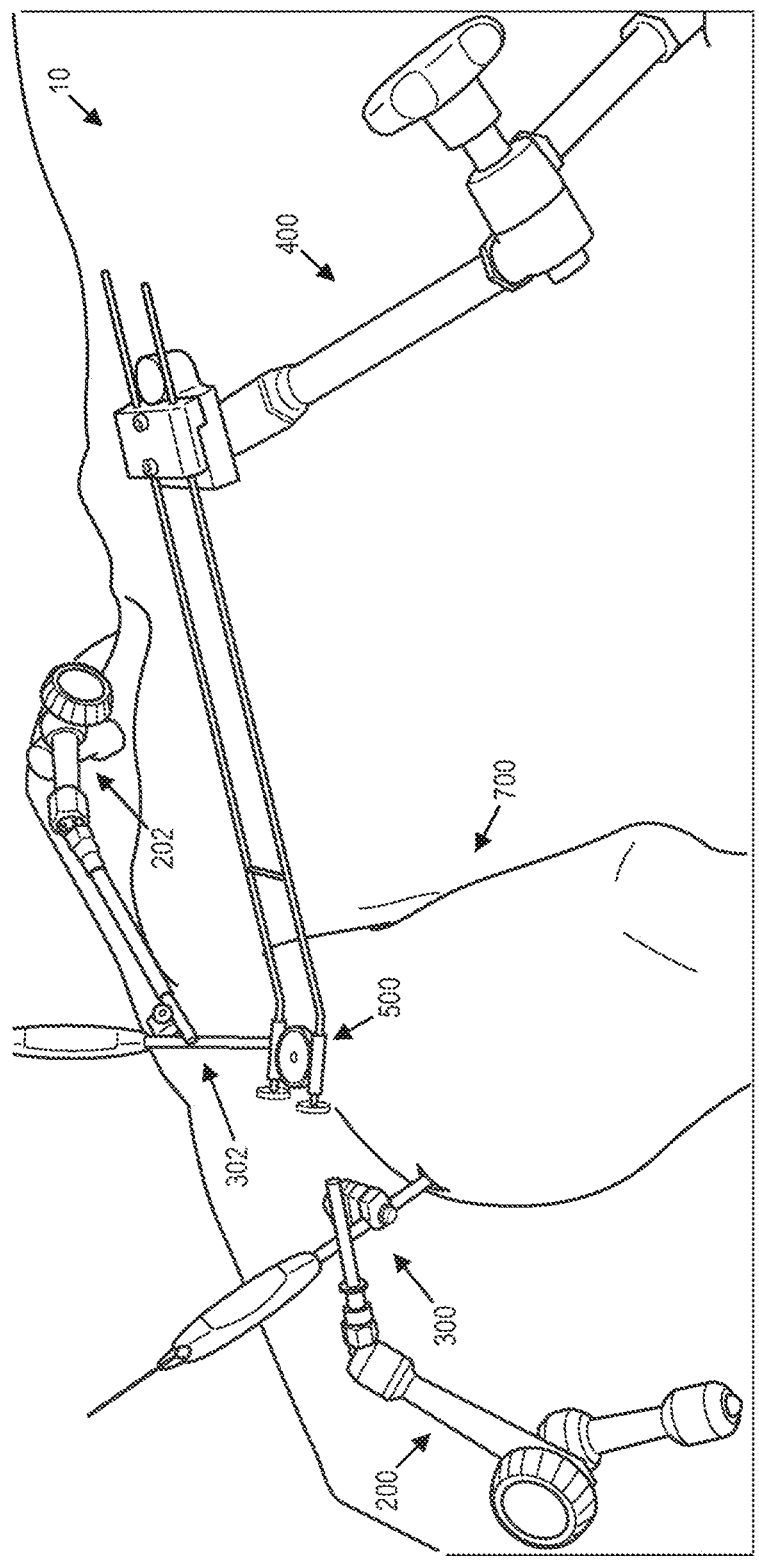
FIG. 2 illustrates a surgical system according to the disclosure as in FIG. 1, but instead includes a cadaveric surgical specimen (partially covered by a surgical blanket) in place of model skeletal section.
Figure 3:
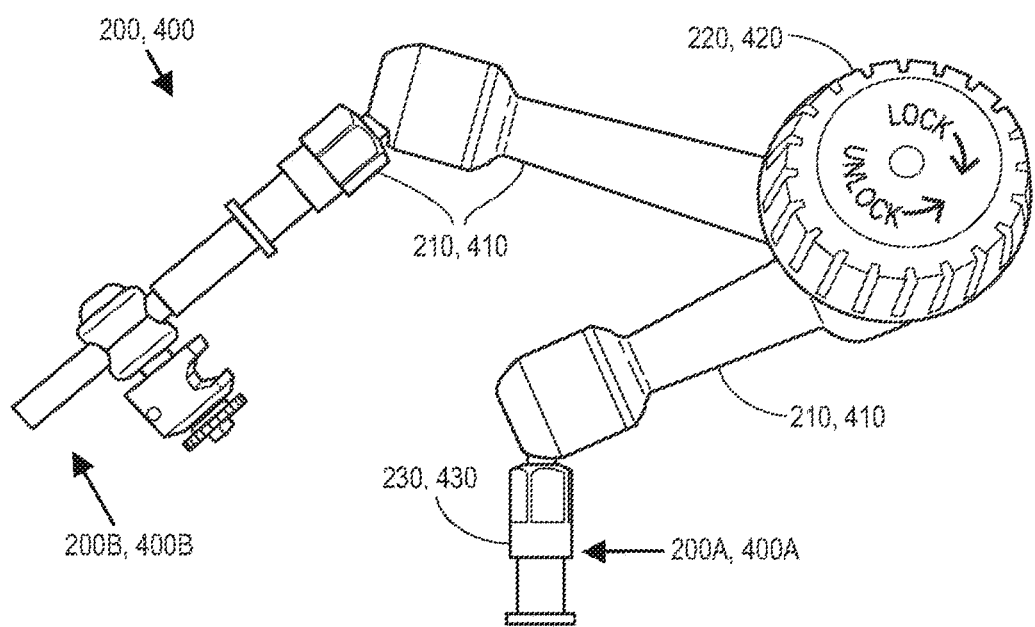
FIG. 3 illustrates an articulated arm according to the disclosure, which can be used as a reduction arm or a fixation arm with corresponding further distal attachments (not shown).

In an aspect, the disclosure relates to a surgical system 10, for example as illustrated in FIGS. 1-3. The surgical system 10 includes a work surface 100, a reduction arm 200 (fixedly) mounted to the work surface 100 at a proximal region (or end) 200A of the reduction arm 200, a reduction handle 300 mounted to the reduction arm 200 at a distal region (or end) 200B of the reduction arm 200, a fixation arm 400 (fixedly) mounted to the work surface 100 at a proximal region (or end) 400A of the fixation arm 400, a fixation drill guide 500 mounted to the fixation arm 400 at a distal region (or end) 400B of the fixation arm, and an image acquisition unit 600 directed toward the work surface 100 (e.g., adapted/positioned to acquire an image of a surgical subject 700 on the work surface 100). The various components of the surgical system 10 can be variously adapted to move (e.g., articulate, such as rotate or translate), attach, and/or lock in place with respect to other components. The reduction arm 200 is articulatable relative to the work surface 100, and the reduction arm 200 is lockable in position relative to the work surface 100. The reduction handle 300 is adapted to attach to a surgical subject 700. The fixation arm 400 is articulatable relative to the work surface 100, and the fixation arm 400 is lockable in position relative to the work surface 100 (e.g., similar mobility and fixability as the reduction arm 200). The fixation drill guide 500 is adapted to receive a fixation screw 710 (e.g., or other fixation means) therethrough for insertion into the surgical subject 700 (e.g., and corresponding drill bit for pin insertion). The image acquisition unit 600 is lockable in position relative to the work surface 100.

The work surface 100 is generally a surgical or other table having two opposing surfaces, including a top surface 110 and bottom surface 120. The work surface 100 and corresponding surgical table preferably are radiolucent to facilitate imaging between an emitter unit 610 and an intensifier unit 620 of the image acquisition unit 600 on opposite sides of the work surface 100 or surgical table. The surgical work area can be the top table surface 110 where a surgical subject 700 is to be placed and defines the general surgical area, such as where the reduction arm 200 and fixation arm 400 operate.

In an embodiment, the work surface 100 is articulatable. The work surface 100 can be generally articulatable relative to a fixed reference surface (e.g., floor of operating room). The work surface 100 can be translatable, for example horizontally (e.g., in x-y plane), vertically (e.g., in z axis), or both. Additionally or alternatively, the work surface 100 can be rotatable or tiltable. The work surface 100 can be used to position-adjust and/or orient the surgical subject 700 in a desired manner relative to the image acquisition unit 600 via remote control of the surge, tilt, roll, and X-Y translation, for example prior to reduction of surgical subject's injured body portion.

Articulation of the arms 200, 400 generally includes any movement relative to the work surface 100, such as rotation, translation, and/or extension. The proximal end 200A, 400A of the reduction or fixation arm 200, 400 is generally fixed in position at the work surface 100, and articulation of the arm 200, 400 components allow the distal end 200B, 400B of the arm 200, 400 to be positioned at a desired 3-dimensional location and orientation relative to the work surface 100 (e.g., above the top surface 110 thereof). Articulation and locking can be performed manually at the arm 200, 400 by a person conducting surgery using the system 10. Articulation and locking can be performed automatically/remotely from the arm 200, 400, such as with a robotic arm (not shown) controlled by a person conducting surgery using the system 10.

After general positioning and orientation of the surgical subject 700 (e.g., via surgical table 100 adjustment), the reduction arm 200 and handle 300 serve to position-adjust and orient a portion of the surgical subject 700 (e.g., the local body portion which is the surgical target area, such as a fractured bone fragment) to a desired position and orientation prior to the surgical procedure, and to maintain the surgical subject 700 in the desired position and orientation during to the surgical procedure. Articulation of the reduction arm 200 and handle 300 is generally performed interactively with the optical imaging system 600 to attain/fix the surgical subject 700 in place prior to fixation of a luxation or fracture.

The reduction handle 300 can temporarily or removably attach to the surgical subject 700. For example, the reduction handle 300 can include a pin 312 (e.g., threaded pin) at a distal location 300B of the handle 300, which pin 312 can be inserted into a bone of the surgical subject 700 prior to fixation, such as by drilling or screwing the pin 312 into the bone. The pin 312 can be at the distal tip of a corresponding reduction rod 310, which can be formed from metal (e.g., stainless steel) or other rigid material. The pin 312 remains fixedly in place during surgery, and then can be removed afterwards (e.g., upon completion of fixation). Attachment to the surgical subject 700 is generally at a reduction location 730 remote from the planned surgical site, yet close enough thereto such that fixing or locking the reduction arm 200 and handle 300 in place correspondingly maintains the surgical site in the desired fixed position and orientation during surgery (fixation). In embodiments where the reduction arm 200 and handle 300 combination is intended to be manually articulated by a person conducting surgery, the reduction handle 300 can include a hand-gripping portion 330 at a proximal location 300A of the handle 300 to be held by the person for manual articulation. In embodiments where the reduction arm 200 and handle 300 combination is intended to be automatically/remotely articulated, such as with a robotic arm, the reduction handle 300 and corresponding pin 312 can be an attachment to or a distal portion of the reduction arm 200 (e.g., a hand-gripping portion is not required).

In some embodiments, multiple reduction arm 200 and handle 300 combinations can be used to position and orient the surgical subject 700. For example, the surgical system 10 can include a first reduction arm 200 with a first reduction handle 300 mounted thereto and a second reduction arm 202 with a second reduction handle 302 mounted thereto, where the first and second reduction arms 200, 202 are mounted to different locations of the work surface 100. In other embodiments, the surgical system 10 only uses a single reduction arm 200 and handle 300 combination to adequately position and orient the surgical subject 700.

In an embodiment, the reduction handle 300 includes a reduction rod 310 with an insertion pin 312 at a distal end of the reduction rod 310, for example as a threaded pin 312 at the end of a rigid rod 310 such as made from stainless steel or other metal. The proximal end of the reduction rod 310 can include an attachment means 314, which can include a threaded portion for receiving a compression or locking nut 326 or a coupler for attachment to a surgical drill. The reduction handle 300 can further include a reduction tube 320 adapted to receive the reduction rod 310 therethrough. The reduction tube 320 can include knurling 324 to facilitate gripping by a user. For example, the reduction tube 320 can be a cylindrical tube or other elongate structure with an open interior volume. The reduction tube 320 can be the point of attachment to the reduction arm 200 and can further include a (hand) gripping portion 330 for manual articulation.

In an embodiment, the reduction tube 320 includes or is formed from a radiolucent material. For example, the reduction tube 320 can be formed from a radiolucent material such as clear or transparent plastic or polymeric material (e.g., acrylic glass), which can be a 3D-printable object and/or disposable after a single use. Formation of the reduction tube 320 from a radiolucent material can limit potential visual obstructions during x-ray imaging, for example where only the thinner reduction rod 310 would provide a potential visible obstruction, such as in the case of stainless steel or other metal rods 310. In other embodiments, the reduction tube 320 can be formed from conventional materials such as stainless steel or other metals.

In an embodiment, the reduction handle 300 can further include a reduction sleeve 340 slidably mounted to an (external) distal end of the reduction tube 320. The reduction sleeve 340 is formed from a flexible material (e.g., soft or rubbery plastic) and has a tapered distal tip 342 with a longitudinal slot 344 and a stress-reduction (e.g., circular) gap 346 (e.g., two or more slots and gaps 344, 346) permitting expansion of the tapered distal tip 342. The reduction sleeve 340 can include knurling 348 to facilitate gripping by a user. The reduction sleeve 340 protects internal soft tissue in the surgical subject from injury, shielding the soft tissue from the threaded tip 312 of a reduction rod 310 as well as distal end of the reduction tube 320, which can have rough edges as anchoring teeth 322. Once inserted into the surgical subject 700 where the distal tip 342 of the sleeve 340 contacts bone, the longitudinal slots 344 expand the tapered distal tip 342, creating an opening for the reduction tube 320 and reduction pin 312 to contact the bone where they will be inserted. The distal tip 342 can likewise contract back to a closed position when the reduction tube 320 and reduction pin 312 are removed.

Figure 10:
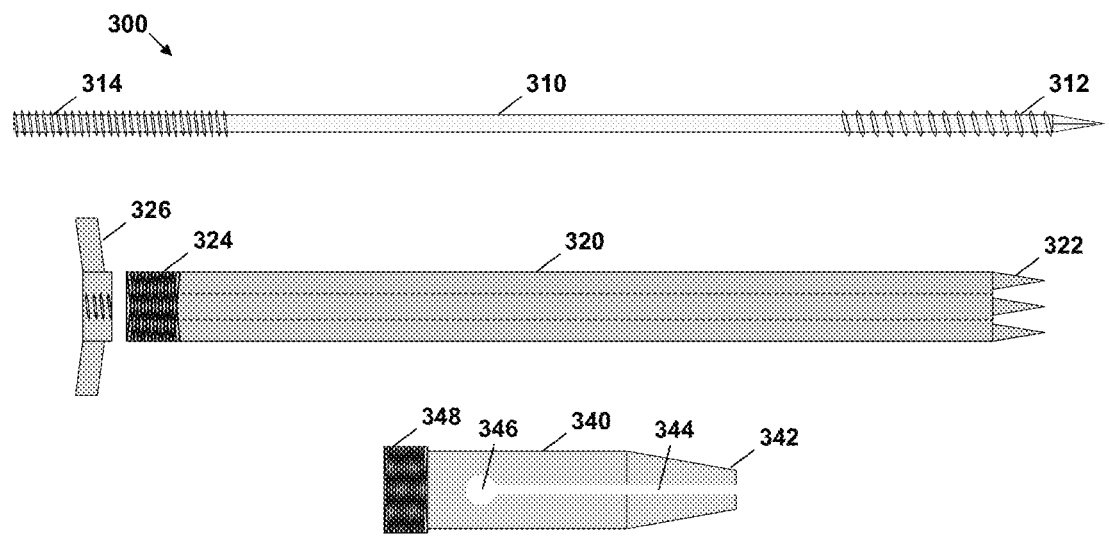
FIG. 10 is a side disassembled view of a reduction handle according to the disclosure.
Figure 11:
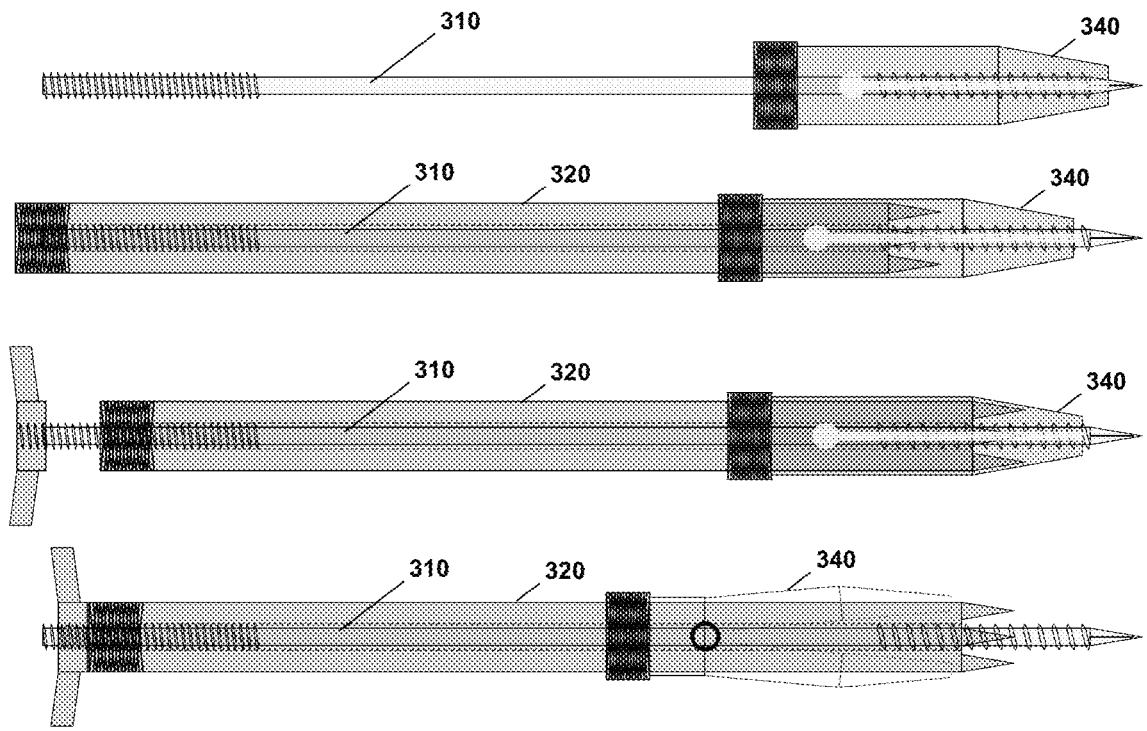
FIG. 11 is a side view of a reduction handle according to the disclosure and at various points of insertion into a surgical subject.

FIG. 10 illustrates disassembled components of the reduction handle 300 as described above, including the reduction rod 310, the reduction tube 320, and the reduction sleeve 340. From top to bottom, FIG. 11 illustrates the reduction handle 300 from FIG. 10 as it is assembled, inserted into the surgical subject 700 soft tissue, and then inserted into bone (e.g., insertion of the reduction pin 312 portion therein). In the bottom panel of FIG. 11, the reduction handle 300 has been fully inserted so that the reduction pin 312 is anchored to bone (not shown), and the nut 326 secures the rod 310 and pin 312 in place. The longitudinal slots 344 have expanded, allowing the sleeve 340 to slide backwards along the reduction tube 320, further exposing the anchoring teeth 322, which can provide additional gripping or anchoring force holding the reduction handle 300 in place against bone.

Figure 12:
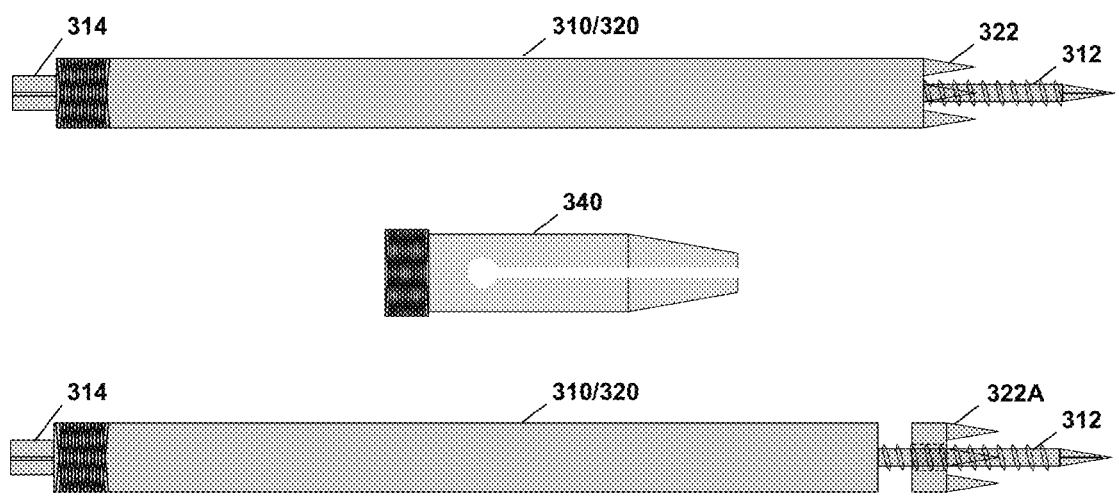
FIG. 12 is a side view of a reduction handle according to additional embodiments of the disclosure.

FIG. 12 illustrates additional embodiments of the reduction handle 300 in which the reduction rod 310 and the reduction tube 320 are a single unitary structure 310/320 in which the rod 310, pin 312, and attachment means 314 portions do not independently rotate relative to the tube 320 portion. The attachment means 314 can be a coupler or other mechanical mating attachment to a surgical drill (not shown), and the sleeve 340 can be slidably mounted to an (external) distal end of the rod/tube 310/320 as in the preceding embodiments. A surgical drill can be used to insert the pin 312 by rotating the unitary rod/tube 310/320 body, and the sleeve 340 can protect tissue upon initial entry and expand upon insertion as described above. The bottom panel of FIG. 12 illustrates a further refinement in which the anchoring teeth 322A are in the form of a freely rotatable washer or other annular attachment fitting over the pin 312. In this case, the anchoring teeth 322A do not rotate when the main rod/tube 310/320 body rotates during insertion, which reduces damage to surrounding tissue from rotating teeth. Once inserted and held in place against the bone, however, the anchoring teeth 322A still can provide additional gripping or anchoring force holding the reduction handle 300 in place against bone.

The fixation arm 400 and drill guide 500 serve to position-adjust and orient the eventual fixation screw 710 (e.g., or other fixation means) such that insertion thereof can be controlled to have the desired insertion location and insertion orientation/angle in the surgical subject 700 during fixation. As specifically illustrated herein, the surgical system 10 and component can be used for proper insertion location and insertion orientation/angle into the sacral body 720 for MIO of SIL/F. The surgical system 10 can be used for reduction and fixation of luxations and/or fractures in other areas where accurate insertion location and orientation are particularly important. For example, the surgical system 10 can be used for reduction and fixation of luxations and/or fractures in long bone injuries, spinal injuries (e.g., between adjacent vertebrae), etc., whether in animal or human patients. Articulation of the fixation arm 400 and drill guide 500 is generally performed interactively with the optical imaging system 600 to attain/fix the drill guide 500 in place after reduction and prior to drilling during fixation. Notably, a temporary fixation pin is generally used with standard MIO but is not needed with the disclosed surgical system 10.

In an embodiment, the fixation arm 400 includes two longitudinally extending retaining members 412 at the distal region 400B of the fixation arm 400 and spaced apart by a distance $D_R$ of at least 1 cm (e.g., at least 1, 1.5, 2, 2.5, 3, or 5 cm and/or up to 2, 2.5, 3, 4, 6, 8, or 10 cm). The fixation drill guide 500 is mounted to the fixation arm 400 between the two longitudinally extending retaining members 412 (e.g., at distal region of the members). The longitudinally extending retaining members 412 can be rods, for example about 1-2 mm in diameter, formed from stainless steel or other metal or rigid material. In particular when the retaining members 412 are radiopaque, the spacing apart of the members 412 reduces their obstruction in the relevant field of view when trying to position and orient the drill guide 500, providing more viewing space to detect and correct off-axis orientation of the drill guide 500 before fixation. Formation of the drill guide 500 from primarily radiolucent materials (e.g., but including radiopaque aiming guides) further reduces obstructions in the field of view. A ring clamp 414 or other receiving/retaining structure can be incorporated between the retaining members 412, such as at a distal portion thereof, to serve as mounting location for the fixation drill guide 500. For example, the fixation drill guide 500 can include a circular disc 540 proximal portion as described below.

In an embodiment, the reduction arm 200 includes at least two reduction arm elements 210 rotatably mounted to each other. Similarly, the fixation arm 400 can include at least two fixation arm elements 410 rotatably mounted to each other. Either or both of the reduction and fixation arms 200, 400 can be 6-axis arms that can be rotated in any direction with respect to each other and that can be locked in position when desired position/orientation is reached, for example with a single locking wheel 220, 420 for each 6-axis arm 200, 400. Although referenced as a "6-axis arm," suitable arms 200, 400 according to the disclosure can have more than 6 axes in ranges of motion, because the articulation structure at the proximal and distal extremes of the arm units can include universal joints.

The combination of (1) the ability to independently articulate and lock the reduction arm/handle 200, 300 combination and fixation arm/drill guide 400, 500 combination into fixed positions relative to the work surface 100, and (2) the ability to maintain the optical imaging system 600 (or image acquisition unit(s) thereof) in a fixed position relative to the work surface 100 allows accurate placement and orientation of the fixation screw 710 in a manner that is safer for both the surgical subject 700, due to the correspondingly more accurate screw/pin placement and orientation in a minimally invasive osteosynthesis (MIO) procedure vs. an open reduction and internal fixation (ORIF) procedure, and the surgical personnel, due to the ability of the surgical personnel to be remote from the surgical subject 700 during x-ray exposure. Fixed positions for each of the reduction arm/handle 200, 300 combination, the fixation arm/drill guide 400,500 combination, and the image acquisition unit 600 relative to the work surface 100 means that initial proper positioning and orientation of the surgical subject 700 during reduction will allow subsequent proper positioning and orientation of the fixation screw 710 in the surgical subject 700 during fixation, such as by visually monitoring the fixation arm/drill guide 400, 500 combination after the reduction arm/handle 200, 300 combination is locked into its fixed, desired position. Namely, prior to fixation, the surgical subject can be position- and orientation-adjusted by one or more of (1) manual adjustment by surgical personnel (e.g., supported in place with vacuum conforming bean bag supports), (2) manual or automated adjustment by movement (e.g., translating and/or tilting) of the work surface 100, and (3) manual or automated adjustment by movement of the reduction handle 300 and corresponding locking in place of the reduction arm 200. Proper positioning and orientation can be confirmed by visually monitoring and adjusting roll and yaw of transverse processes during lumbosacral alignment in between incremental adjustments (e.g., when surgical personnel are a safe distance away from the imaging unit 600). The fixed position of the image acquisition unit 600 during the process means that visual positioning of the fixation arm/drill guide 400, 500 combination will result in the proper insertion location and orientation of the fixation screw 710, if the surgical subject 700 has been properly positioned and oriented (as confirmed by visual monitoring) as well as locked or fixed in place during reduction.

The image acquisition unit 600 can be a component of an optical imaging system including associated hardware, software, electronics, etc. In an embodiment, the image acquisition unit 600 is not adjustable or otherwise moveable as part of its normal operation, and it remains in a locked or fixed position relative to the work surface 100 and to a fixed reference surface (e.g., floor of operating or other surrounding room). In another embodiment, the image acquisition unit 600 is adjustable or otherwise moveable as part of its normal operation, but it can be placed into a locked or fixed position relative to the work surface 100 and to a fixed reference surface, for example for the entire surgical procedure or after reduction but before fixation.

In an embodiment, the image acquisition unit 600 is an x-ray imaging unit (e.g., as a component of a C-arm x-ray imaging system). There are two common types of C-arm imaging units: small and large units (e.g., variable size and power). Small units are most often used for extremities (e.g., foot, hand) and usually placed over the surgical work table or on its side. These could be used for small dogs and cats in SIL cases. Large units are placed with the arm spanning the surgical work table 100 across the table as described herein. These are more powerful and therefore are good for any body part, in particular the thicker body parts (e.g., pelvis). The drawback of the larger units is more radiation exposure, but this drawback is mitigated by the disclosed surgical system 10 with the ability for the surgical personnel to move a safe distance away from the work surface 100 and emitter unit 610 during operation of the imaging unit 600. Other image acquisition units are possible. A portable X-ray machine with standard cassettes that are processed elsewhere (e.g., on a unit affixed to the machine) can be used. Intraoperative computed tomography (CT) imaging using a small CT unit or a mechanized C-Arm). Such units provide immediate 3D images as well as 3D multiplanar reconstructed views (e.g., which can be used measure and calculate screw angles postoperatively as described in the examples below).

In an embodiment, the image acquisition unit 600 includes an emitter unit 610, such as an x-ray tube or other source of emitted x-rays for imaging, and an intensifier unit 620, such as a receiver or image intensifier to convert incident x-rays to visible light of sufficient intensity to provide a viewable image. The emitter unit 610 and the intensifier unit 620 can be components of a C-arm x-ray imaging system. In a suitable arrangement, the emitter unit 610 is positioned above the work surface 100, which is the same area where the reduction arm/handle 200, 300 and the fixation arm/drill guide 400, 500 are adapted to articulate, and the intensifier unit 620 is positioned below the work surface 10, generally opposing the emitter unit 610 and beneath the work surface/surgical table 100. This relative orientation of the emitter/intensifier 610, 620 provides a better image quality as compared to the reverse orientation, and the corresponding use of the reduction arm/handle and fixation arm/handle limit x-ray exposure of the surgical personnel. This orientation/positioning of the image acquisition unit 600 is generally referenced as an inverted position. It can be used as it provides better image quality, but it significantly increases radiation exposure (direct and backscatter) to sensitive body regions (e.g., eyes, thyroid, face in general). As noted above, however, the surgical system 10 allows use of the inverted position to obtain good radiographic images without radiation exposure due to the ability of surgical personnel to move a safe distance away from the radiation while the surgical system 10 holds the surgical subject 700 in a fixed position and orientation. In contrast to the inverted position, the normal recommended position of the C-arm unit 600 has the emitter 610 below the work table 100 and the intensifier unit 620 above and away from the patient, which results in a poor image with much magnification/distortion. To reduce this distortion in the recommended position, surgeons must lower the C-arm and bring the intensifier close to the body. The resulting problems then are then: a time consuming process, a risk of contamination to the surgical site, and less/limited space for the surgeon to maneuver and operate surgical instruments.

In an aspect, the disclosure also relates to a method for minimally invasive osteosynthesis of sacroiliac luxations/fractures. The method includes placing a surgical subject 700 (e.g., animal or small animal, such as dog or cat) on the work surface 100 of the surgical system 10. The reduction handle 300 is then attached to the surgical subject 700, for example by drilling or inserting a reduction pin 312 or rod into a support bone in the surgical subject 700 at a reduction location 730, suitably after initially positioning and/or orienting the subject 700 with work surface 100 position adjustment. The portion of the surgical subject 700 which is to be the target of surgery is then positioned and oriented the using the reduction arm 200 and the reduction handle 300, thereby reducing a fracture or other injury for fixation. Adjustment of the reduction arm 200 and handle 300 can be performed manually by a user or automatically/remotely using a robot arm, controlled by a user. The surgical subject 700 as a whole generally has been previously positioned using the position-adjustable work surface or surgical table 100, and the surgical subject can be readjusted as needed after reduction. Proper position and orientation of the surgical subject 700 is then visually confirmed using the image acquisition unit 600, for example by visually confirming proper roll and yaw positioning of transverse processes for lumbosacral alignment in a MIO SIL/F procedure. The reduction arm 200 is then locked in place relative to the work surface 100, which similarly locks the reduction handle 300 and the surgical subject 700 at the point of attachment for the reduction location 730 in place relative to the work surface 100. The fixation drill guide 500 is then inserted into the surgical subject 700 at a position 720 for minimally invasive osteosynthesis of a sacroiliac luxation or fracture in the surgical subject 700. The fixation drill guide 500 is then positioned and oriented using the fixation arm 400, for example manually by a user or automatically/remotely using a robot arm, controlled by a user. Proper position and orientation of the fixation drill guide 500 are then visually confirmed using the image acquisition unit 600. Such confirmation can include visually confirming proper (i) position or location where initial insertion of lag screw 710 will occur in the sacral body 720 and (ii) orientation or angle of entry for the lag screw 710 such that the lag screw 710 remains substantially on-axis and within the sacral body 720 upon full insertion (i.e., without substantial egress of the lag screw 710 from the sacral body 720 into neighboring areas, which could cause injury to the surgical subject 700 and/or result in insufficient fixation. The lag screw 710 is inserted into the sacral body 720 and more specifically the safe implantation corridor of the sacral body 720. That safe corridor can be generally defined as (1) medullary canal dorsally, (2) L7-S1 disc space cranially, and (3) sacral ventral cortex ventrally. The corridor should be parallel to the cranial end plate of the sacrum. The fixation arm 400 is then locked in place relative to the work surface 100, which similarly locks the fixation drill guide 500 in place relative to the work surface 100. A fixation screw 710 is then inserted (e.g., drilled) through the fixation drill guide 500 and into the surgical subject 700, in particular into the sacral body 720 of the surgical subject 700 with proper position and orientation for minimally invasive osteosynthesis of the sacroiliac luxation or fracture in the surgical subject 700. Subsequent steps can include removing/disengaging the reduction handle 300 and drill guide 500, and then closing the corresponding insertion wounds, etc.

In an embodiment, positioning and orienting the surgical subject 700 using the reduction arm 200 and the reduction handle 300 can include a series of iterative adjustments. First, at least one of a position and an orientation of the surgical subject 700 (or a body portion thereof based on reduction location) is adjusted using the reduction arm 200 and handle 300. The reduction arm 200 is then locked in place relative to the work surface 100, and then the current position and orientation of the surgical subject 700 is visually interrogated using the image acquisition unit 600. The iterative adjusting, locking, and interrogating steps can be repeated until proper position and orientation of the surgical subject 700 are achieved, in particular with respect to the specific surgical site in the subject 700.

In an embodiment, inserting the fixation drill guide 500 into the surgical subject 700 can include locating an insertion point using the image acquisition unit 600 and an externally positionable radiopaque location marker. The radiopaque location marker can be a radiopaque washer or other annular device placed on the outside of the surgical subject 700 body before insertion of the fixation drill guide 500. The location marker can be repositioned until the open center of the location marker is determined to be positioned above the sacral body 720 by visual interrogation using the image acquisition unit 600. Once the insertion point is location, the fixation drill guide 500 is inserted into the surgical subject 700 at the insertion point.

In an embodiment, positioning and orienting the fixation drill guide 500 using the fixation arm 400 can include a series of iterative adjustments. First, at least one of a position and an orientation of the fixation drill guide 500 is adjusted using the fixation arm 400. The fixation arm 400 is then locked in place relative to the work surface 100, and the current position and orientation of the fixation drill guide 500 in the surgical subject 700 is visually interrogated using the image acquisition unit 600. The iterative adjusting, locking, and interrogating steps can be repeated until proper position and orientation of the drill guide 500 are achieved. In another embodiment, the fixation drill guide 500 is a minimally invasive lucent aiming device and drill guide as described below. In such case, visually confirmation of proper position and orientation of the fixation drill guide 500 using the image acquisition unit 600 includes confirming that the proximal aiming guides 520 are aligned on axis with the distal aiming guides 530 of the fixation drill guide 500.

In another aspect, the disclosure relates to a minimally invasive lucent aiming device and drill guide 500. The aiming device 500 includes a drill guide sleeve 510 defining a longitudinal axis Z therethrough which is adapted to receive a fixation screw 710 therethrough for insertion into a surgical subject 700 (e.g., and corresponding drill bit for pin insertion). The drill guide sleeve 510 can be a tube or other elongate structure with an open interior volume, for example with a cylindrical cross section. The aiming device 500 further includes at least two radially extending radiopaque proximal (or cis or near) aiming guides 520 positioned at different angular positions (θ) and extending outwardly from a proximal (or cis or near) end 510A of the drill guide sleeve 510. The proximal end 500A of the device 500 can be referenced as the outer portion, as it is not inserted into the surgical subject 700 during a procedure. The aiming device 500 further includes at least two radially extending radiopaque distal (or trans or far) aiming guides 530 positioned at different angular positions (θ) and extending outwardly from a distal (or trans or far) end 510B of the drill guide sleeve 500. The distal end 500B of the device 500 can be referenced as the inner portion, as it is inserted into the surgical subject 700 during a procedure. The angular position (θ) for each proximal aiming guide 520 is the same as the angular position (θ) for a corresponding distal aiming guide 530. More specifically, the proximal aiming guides have different angular positions (θ) relative to each other, and the distal aiming guides 530 have different angular positions (θ) relative to each other, but corresponding pairs of aiming guides 520, 530 at opposing ends of the drill guide sleeve 510 have the same angular positions. This pairing of corresponding angular positions (θ) is what allows off-axis orientation of the drill guide 500 to be visually detected and corrected. In a first illustrative embodiment and as shown in FIGS. 4-7, there are four proximal aiming guides 520 at angular positions (θ) of 0°, 90°, 180°, and 270°, and there are four corresponding distal aiming guides 530 at corresponding angular positions (θ) of 0°, 90°, 180°, and 270° (i.e., four orthogonal guides at each end). In a second illustrative embodiment, there are three proximal aiming guides 520 at angular positions (θ) of 0°, 120°, and 240°, and there are three corresponding distal aiming guides 530 at corresponding angular positions (θ) of 0°, 120°, and 240°. In a third illustrative embodiment, there are two proximal aiming guides 520 at angular positions (θ) of 0° and 90°, and there are two corresponding distal aiming guides 530 at corresponding angular positions (θ) of 0° and 90° (i.e., two orthogonal guides at each end). In a fourth illustrative embodiment, there are three proximal aiming guides 520 at angular positions (θ) of 0°, 120°, and 240°, and there four distal aiming guides 530. Three of the distal aiming guides 530 have corresponding angular positions (θ) of 0°, 120°, and 240°, and the fourth distal aiming guide 530 can be at any angular position (θ), since it has no counterpart. In a fifth illustrative embodiment, there are three proximal aiming guides 520 at angular positions (θ) of 0°, 90°, and 180°, and there are three distal aiming guides 530 at angular positions (θ) of 0°, 90°, and 270° (i.e., two corresponding guide pairs at 0° and 90°, with the other guides having no counterparts). At least two aiming guides 520, 530 on each proximal and distal end is preferable, with more than two each being more preferable. In an embodiment, however, there can be a single proximal/distal aiming guide pair 520, 530.

In an embodiment, the aiming device and drill guide 500 further includes a radiolucent body 540 enclosing or attached to the proximal aiming guides 520 and positioned at the proximal end 510A of the drill guide sleeve 510. The radiolucent body 540 can be a thin circular disc, rectangular shape, or other cross sectional shape, for example having a thickness in a range from 1 mm to 10 mm, such as least 1, 1.5, 2, 2.5, 3, or 5 mm and/or up to 2, 2.5, 3, 4, 6, 8, or 10 mm. The radiolucent body 540 can be formed from clear or transparent plastic or polymeric material (e.g., acrylic), which can be molded or a 3D-printable object. The radiolucent body 540 can be a separate structure that is mounted or attached to the drill guide sleeve 510, such as a clear plastic disc 540 mounted to a metal drill guide sleeve 510. The radiolucent body 540 can be integrally formed with the drill guide sleeve 510, for example being a unitary body including the radiolucent body 540 and drill guide sleeve 510 portions, such as formed from a plastic material by a molding or 3D printing process. In another embodiment, the radiolucent body 540 can be absent, and the proximal aiming guides 520 can simply extend outwardly from the drill guide sleeve 510, for example from a ring-type structure mounted to the drill guide sleeve 510, for example similar to the illustrated embodiment with the distal aiming guides 530.

In an embodiment, each corresponding pair of proximal aiming guides 520 and distal aiming guides 530 have relative lengths (l) and widths (w) (or diameters) such that one aiming guide is longer and narrower than the corresponding opposing aiming guide in the pair. More specifically, one aiming guide is relatively long and narrow, and the other aiming guide is relatively shorter and wider. The different lengths (l) and widths (w) provide a visual contrast between the opposing aiming guides even when the drill guide is perfectly aligned on axis. In a further embodiment, the proximal aiming guide 520 is longer and narrower than the corresponding distal aiming guide 530 in the pair. Preferably, the distal aiming guide 530 is the shorter guide, extending outwardly from the drill guide 500 by the smaller length/distance, because the distal end 500B is the portion inserted into the surgical subject 700 body, and smaller/shorter guides create less potential to induce injury in the surrounding body tissue of the surgical subject 700.

In an embodiment, the proximal aiming guides 520 have lengths (l) in a range from 0.5 cm to 5 cm, for example at least 0.5, 1, 1.5, 2, or 2.5 cm and/or up to 1, 1.5, 2, 3, 4, or 5 cm. The distal aiming guides 530 can have lengths (l) in a range from 0.5 mm to 5 mm, for example at least 0.5, 1, 1.5, 2, or 2.5 mm and/or up to 1, 1.5, 2, 3, 4, or 5 mm). The proximal aiming guide 520 length can roughly correspond to the radius of the radiolucent body 540, when present. For example, the radiolucent body 540 can have width or diameter in a range from 1 cm to 10 cm, for example at least 1, 1.5, 2, 2.5, 3, or 5 cm and/or up to 2, 2.5, 3, 4, 6, 8, or 10 cm. In an embodiment, the drill guide sleeve 510 defines an open interior volume having a width D in a range from 1 mm to 10 mm, for example at least 1, 1.5, 2, 2.5, 3, or 5 mm and/or up to 2, 2.5, 3, 4, 6, 8, or 10 mm. The width D can correspond to (internal) diameter for a sleeve 510 with an internal open circular cross section. The width D is generally selected to accommodate the corresponding fixation screw 710 and/or drill. In an embodiment, the drill guide sleeve 510 has a length L in a range from 1 cm to 10 cm, for example at least 1, 1.5, 2, 2.5, 3, or 5 cm and/or up to 2, 2.5, 3, 4, 6, 8, or 10 cm. The length L corresponds to the distance between opposing open ends of a generally straight elongate sleeve structure where the pin and drill bit enter/exit the drill guide. The foregoing dimensions are representative of an aiming device 500 that is appropriately sized for animals such as dogs as well as other small animals, such as cats. The foregoing dimensions and ranges may be suitably adjusted for differently sized (e.g., larger) patients, whether animals or humans.

In an embodiment, the drill guide sleeve 510 includes or is formed from a radiolucent material. The drill guide sleeve 510 can be formed from a radiolucent material such as clear or transparent plastic material (e.g., acrylic), which can be a molded or 3D-printable object and/or disposable after a single use. Formation of the drill guide sleeve 510 from a radiolucent material can limit potential visual obstructions during x-ray imaging of the proximal and/or distal aiming guides 520, 530 when the drill guide sleeve 510 is off-axis. In other embodiments, the drill guide sleeve 510 can be formed from conventional materials such as stainless steel or other metals.

EXAMPLES

The examples illustrate the disclosed apparatus and methods, but are not intended to limit the scope of any claims thereto. In particular, the examples include illustrative embodiments of the disclosed surgical system, associated instrumentation, including drill guide and aiming device, and related methods for use thereof.

Example 1: Surgical System

Introduction: Minimally invasive osteosynthesis (MIO) under fluoroscopic guidance has been shown to be a valid treatment modality for lag screw fixation of canine and feline sacroiliac luxation/fractures (SIL/F). This technique however is associated with limitations, including the use of intra-operative ionizing radiations. Furthermore, the narrowness of the safe sacral implantation corridor and its proximity to neurovascular structures leave little room for aiming error during drilling. To achieve consistent, optimal results with MIO of SIL/F, a procedure designed to provide stable reduction and accurate screw placement while reducing exposure to radiation is warranted. This example illustrates surgical system instrumentation and a surgical technique to achieve this goal.

Example 1 and corresponding FIGS. 1-3 illustrate a surgical system 10 according to the disclosure. Surgical system instrumentation and corresponding surgical techniques were devised to optimize screw placement while reducing radiation exposure during minimally invasive osteosynthesis (MIO) via lag screw fixation of sacroiliac luxation/fractures (SIL/F). The surgical system 10 includes at least two variable friction 6-axis arms 200, 400 dedicated to either reduction (reduction arm 200) or fixation (fixation arm 400), a reduction handle (or joystick) 300, and a modified drill guide 500.

A joystick 300 inserted in the ischial tuberosity is used as a reduction aid. Once adequate reduction has been fluoroscopically confirmed, the joystick 300 is secured to its assigned reduction arm 200. Fluoroscopic sacral body location is facilitated by moving a washer above the skin of a surgical subject 700. A modified drill guide 500 secured to the fixation arm 400 is inserted through a stab incision and manipulated until it appears as a circle over the sacral body 720. Sacral pilot and iliac glide holes are drilled prior to lag fixation and skin closure. Subjective evaluation of screw 710 placement and SIL/F reduction is performed on orthogonal pelvic radiographs. Objective measurements of sacral screw 710 orientation and sacral purchase are obtained on CT MPR images.

The 6-axis arms 200, 400 provide stable SIL/F reduction and drill guide 500 alignment throughout surgery, surgical personnel may step away from the patient during fluoroscopic imaging which drastically reduces radiation exposure. Additionally, rigidly securing the drill guide 500 to a dedicated fixation arm 400 virtually eliminates aiming bias during drilling. Evaluation of the system 10 showed accurate sacral screw placement and purchase in all cases, supporting a cadaveric study that demonstrated the superiority of MIO treatment of SIL/F compared to ORIF.

Patient Positioning: The patient or surgical subject lays in lateral recumbency over a radiolucent surgical table allowing multi planar/axial remote positional adjustments. After cursory spinal alignment by means of a conforming vacuum bag, sacral body alignment is adjusted under fluoroscopic guidance using the table's directional controls. Accurate sacral position is achieved when superimposition of L7 transverse processes (dorsoventral roll) and parallelism of L7-S1 end plates (craniocaudal yaw) are ascertained. Specifically, rotation of the sagittal plane about an axis passing through the L7/S1 space is used to control the craniocaudal yaw until parallelism of L7-S1 end plates is attained. Similarly, dorsal plane rotation around a craniocaudal axis passing through the spinal canal controls the dorsoventral roll until superimposition of L7 transverse processes is achieved. This places the sacrum in an optimal position with the transverse axis of the sacral body parallel to the X-ray beam. Patient positioning is adjusted as needed throughout surgery and confirmed using fluoroscopic imaging prior to drilling.

Instrumentation: The surgical instrument system 10 includes two 6-axis articulated arms 200, 400 clamped to a radiolucent surgical table 100 and dedicated to SIL/F reduction and fixation respectively, reduction handle(s) or joystick(s) 300 linked to the reduction arm 200 via a custom post and double clamp, and a modified long-handle drill guide 500 connected to the fixation arm 400 via a custom designed cradle and quick release coupling. The variable-friction 6-axis arms 200, 400 allow the surgeon to 1) precisely control the location and orientation of the joystick(s) 300 and drill guide 500 in three dimensions, and 2) firmly stabilize these instruments once in their desired position.

Reduction: A joystick 300 secured to the ischial tuberosity (or greater trochanter) is used to incrementally mobilize the hemipelvis until SIL/F reduction is ascertained fluoroscopically. The joystick 300 is then rigidly secured to the reduction arm 200, thus providing stable reduction throughout surgery without the need for temporary K-wire fixation. A second joystick 300 inserted in the iliac wing may be used to facilitate reduction.

Fixation: The sacrum is localized by sliding a washer above the skin of the surgical subject 700 until it is centered over the sacral body 720 on fluoroscopic images. The modified drill guide 500, secured to the fixation arm 400, is moved over a stab incision through the gluteal musculature and then inserted into the wound. The guide 500 is manipulated until it appears as a circle centered over the sacral body 720. With the fixation arm 400 locked to rigidly secure the drill guide 500 in position, appropriately sized drill sleeves and bits are used to sequentially drill the sacral pilot and iliac glide holes. The pilot hole is tapped as needed before tightening a washer-loaded screw to complete lag fixation prior to skin closure.

Postoperative Evaluation: Subjective sacral screw placement and SIL/F reduction are evaluated on orthogonal pelvic radiographs. Objective measurements of screw orientation and sacral purchase in the transverse and dorsal planes are obtained on CT MPR images. In a test surgery, a SIL/F was reduced and stabilized with a 6.5 mm lag screw and washer while the long oblique iliac fracture was fixed with two double loop cerclage wires. Subjective evaluation shows near anatomical reduction of the fractures and adequate screw placement. Objective measurements of the dorsoventral (2.3°) and craniocaudal) (2.0°) screw angles, as well as sacral purchase (100% of sacral width) are obtained on CT MPR images. Evaluation of clinical cases showed proper screw orientation and purchase in all cases.

Clinical Application: The surgical system 10 and surgical technique described in this example address limitations associated with MIO of SIL/F, including protection against radiations, safe maintenance of SIL/F reduction throughout surgery, and reliable, accurate sacral screw placement.

According to ALARA principles, distance from the X-ray source is the most effective radiation protection. Stable SIL/F reduction and drill guide alignment provided by the 6-axis arms allows surgical personnel to step away from the patient during fluoroscopic imaging. This simple approach uses the "inverse square law" (i.e., radiation dose decreases with the square of the distance to the X-ray source) to drastically reduce surgical personnel exposure to direct and scattered radiations.

Sacrum localization is traditionally performed by evaluating the relative position of a K-wire inserted in the gluteal musculature. The often linear fluoroscopic projection of the K-wire and its susceptibility to soft tissue manipulation make accurate sacral identification time consuming and challenging. In contrast, moving a flat surgical washer above the skin until it appears centered over the sacral body is a fast, accurate and non-invasive technique.

Current MIO techniques may still result in screw malalignment due to technical challenges. Loss of guide alignment, particularly with unstable SIL/F, may occur as surgeons attempt to simultaneously maintain manual SIL/F reduction as well as drill guide position and orientation. Rigidly securing the SIL/F and drill guide to dedicated arms considerably reduces human error. Indeed, stabilizing the pelvis with the surgical system eliminates the need for temporary fixation with K-wires. Furthermore, once accurate drill guide alignment has been fluoroscopically confirmed, locking the arm in position virtually eliminates aiming bias during drilling.

Example 2: Minimally Invasive Lucent Aiming Device (MILAD)

Example 2 illustrates a minimally invasive lucent aiming device and drill guide according to the disclosure. The aiming device provides timely, accurate, reliable and safe targeting of the sacral body. The purpose of the aiming device is to optimize screw position over the sacral body as well as screw orientation within a safe sacral corridor, while minimizing soft tissue dissection, reducing radiation exposure as well as operating time. The aiming device can incorporated as a fixation drill guide in the general surgical system also disclosed herein (e.g., coupled to a variable-friction 6-axis fixation arm as illustrated in FIGS. 1-3). While originally intended for the MIO treatment of SIL/F, the aiming device could be used for other surgical applications whenever accurate targeting may be needed, whether in a human patient or in an animal surgical subject, for example in patients or subject of different sizes (e.g., other than small animals such as cats and dogs), and/or in anatomical locations other than the sacral body where accurate screw placement and orientation are desired.

Figure 4:
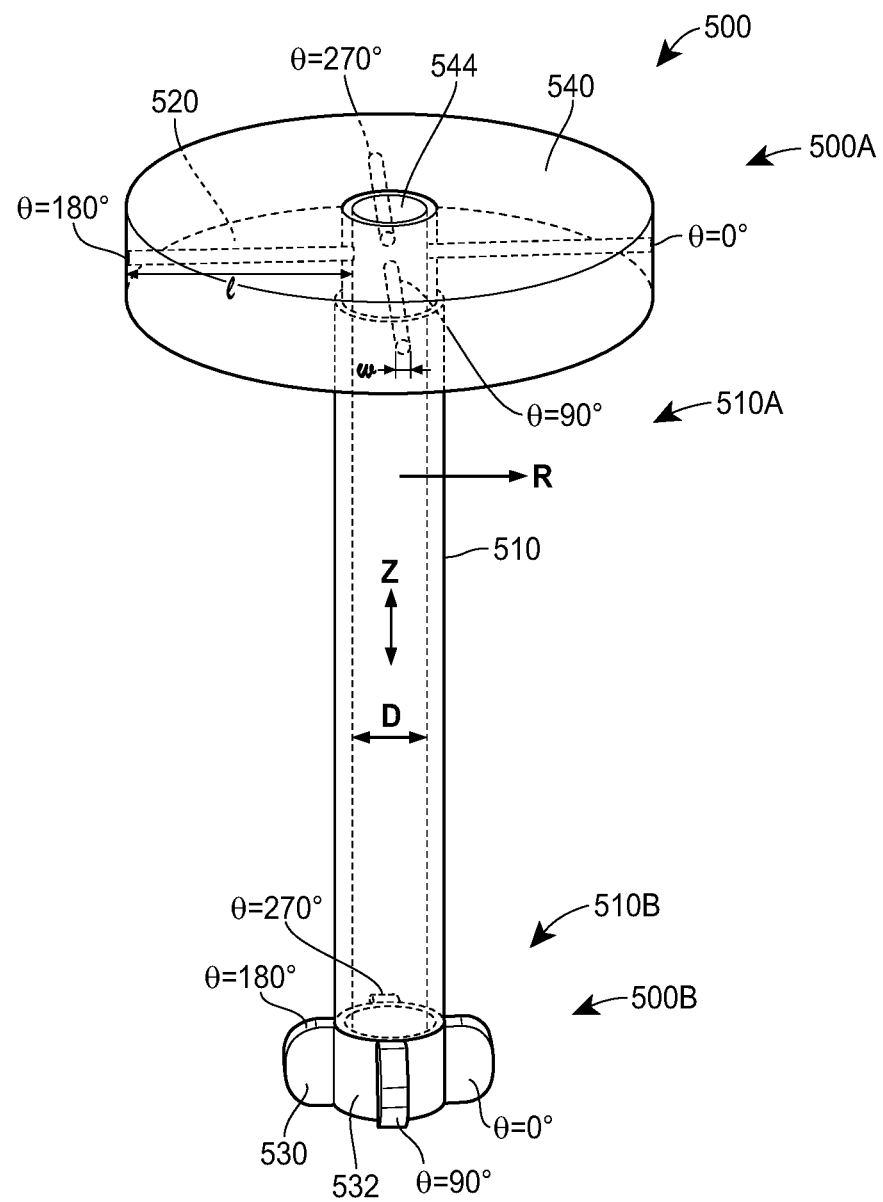
FIG. 4 illustrates a front perspective view of an aiming device according to the disclosure, including a radiolucent acrylic disk with four metal wires as proximal aiming guides, a central sleeve manufactured from radiopaque or radiolucent materials, and a metal sleeve with four fins as distal aiming guides.
Figure 5:
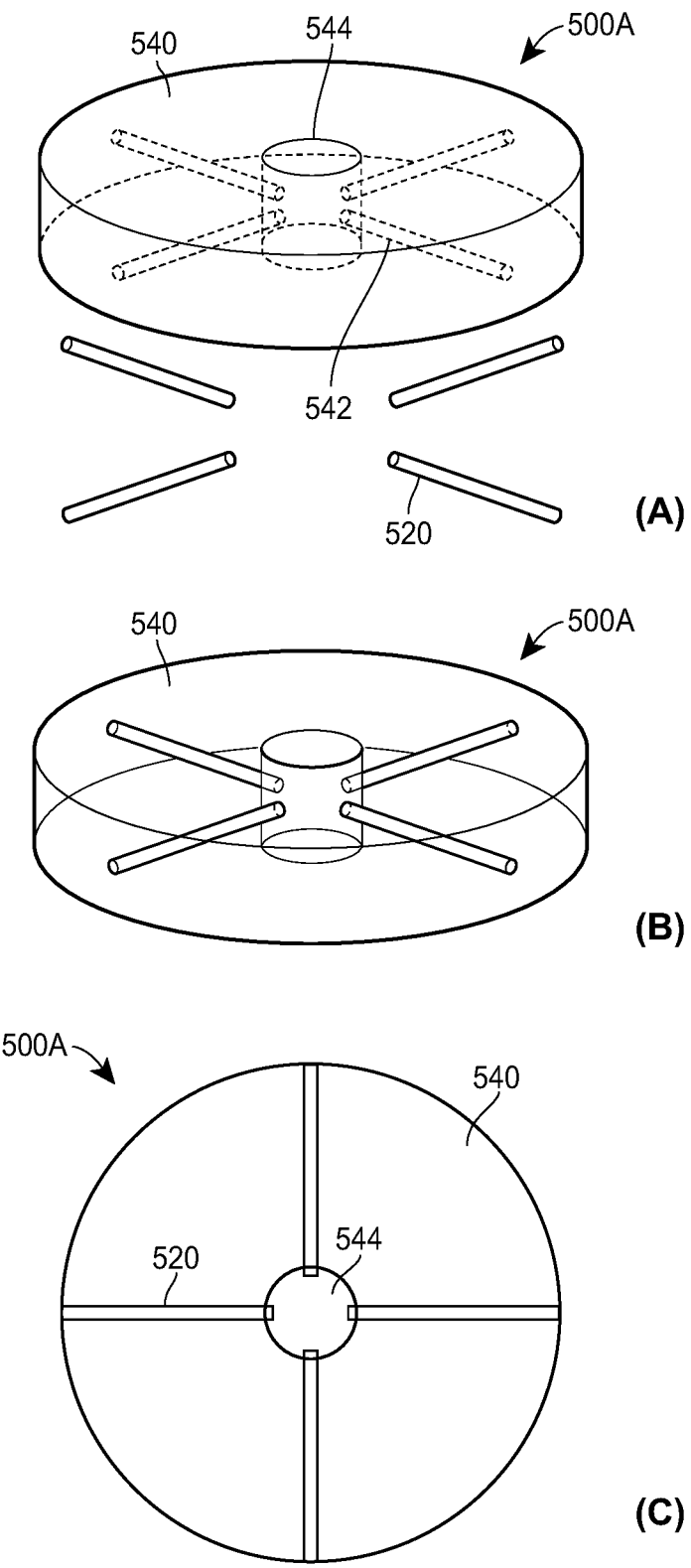
FIG. 5 illustrates the proximal portion of an aiming device according to the disclosure, including a radiolucent acrylic disk with four metal wires used as an upper targeting sight or aiming guides. Panel (A) is an exploded perspective view, panel (B) is a normal (unexploded) perspective view, and panel (C) is a top view.
Figure 6:
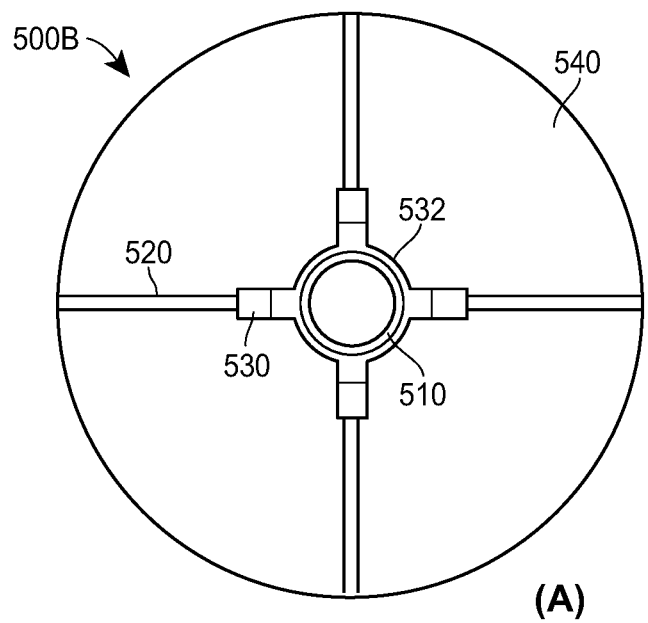
FIG. 6 illustrates the distal portion of an aiming device according to the disclosure, including a thin and short radiopaque metal sleeve that features four orthogonal squat rounded fins or distal aiming guides. Panel (A) is bottom view of the aiming device, panel (B) is a perspective view of the metal sleeve and fins, and panel (C) is a top view of the aiming device.
Figure 6:
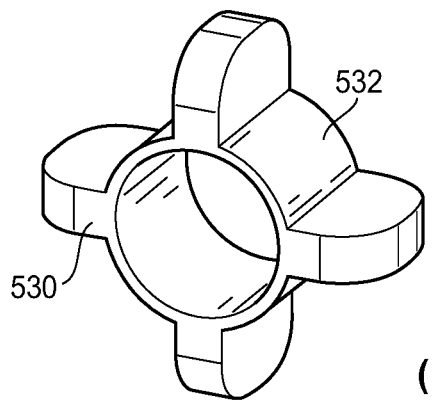
Figure 6:
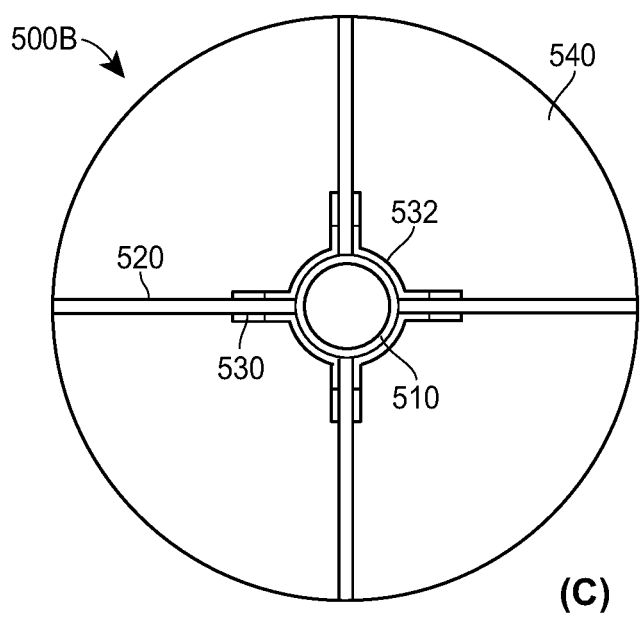

FIGS. 4-6 illustrate a specific embodiment of an aiming device 500 according to the disclosure as well as components thereof, but the aiming device may include other features.

A proximal portion 500A (or upper, near, or cis portion) of the aiming device 500 can include a radiolucent disk or body 540 including four orthogonal thin channels 542 converging toward a central hole 544 (FIGS. 4-6). This disk 540 can be made of any radiolucent material such as poly(methyl methacrylate) (PMMA or acrylic glass, such as PLEXIGLAS) or polyether ether ketone (PEEK). Acrylic glass, being a transparent as well as a radiolucent material, would be suitable in surgical settings. The distal portion 500A further includes four proximal radiopaque steel wires or aiming guides 520 inserted in the channels 542 of the disk 540. This proximal portion 500A is designed to remain outside of the surgical wound and provides an unobstructed view of the sacrum on intra-operative fluoroscopic images. Similar to the sighting scope of a rifle, the aiming guides 520 appear as a cross-hair that can be used to target the sacral body.

A central component of the aiming device 500 includes a drill guide sleeve 510 (FIG. 4). The central component includes of a thin cylindrical tube or sleeve 510 that is press fitted at the proximal end 510A of the sleeve 510 in the central hole 544 of the acrylic disk 540 and oriented perpendicular to its surface. The sleeve 510 may be made of any radiopaque material including, but not limited to, surgical grade stainless steel. Alternatively, the sleeve 510 maybe made of radiolucent hard material such as PEEK. The far or distal end 510B of the sleeve features a circumferential recess 512 that serves as a base for the third aiming device 500 component 530 described below. During surgery, the distal end 510B of the sleeve 510 is inserted in the gluteal muscles through a vertical stab incision extending from the skin to the iliac wing over the sacrum.

A distal portion 500B (or lower, for, or trans portion) of the aiming device 500 can include a thin and short radiopaque sleeve 532 (e.g., metal sleeve such as surgical grade stainless steel) that features four orthogonal squat rounded fins or distal aiming guides 530 (FIGS. 5-6). The sleeve 532 is press fitted around the far recess 512 of the central sleeve 510 so that the fins 530 are aligned with the aiming guides 520 (or crosshair) on the acrylic disk 540 (FIG. 6, panes (A) and (B)). The fin-loaded sleeve 510/532 behaves similarly to the front sight on a rifle to provide unobstructed, fast and accurate alignment of the drill sleeve 510 over the safe sacral corridor.

The assembled aiming device 500 is shown in FIG. 4. The assembled aiming device 500 includes the radiolucent acrylic disk 540 with four metal wires as proximal aiming guides 520, the central sleeve 510 manufactured from radiopaque or radiolucent materials, and the metal sleeve 532 with four fins as distal aiming guides 530. As assembled, the (acrylic) radiolucent disk or body 540 of the aiming device 500 can be secured to a circular tubular clamp 414 (FIG. 2). The clamp 414 side bolts are extended to provide a rail-like sliding handle 412. Using a quick coupling device, the handle 412 is connected to the variable-friction 6-axis fixation arm 400 as used in the corresponding surgical system.

The aiming device 500 was used as an aiming device and drill guide in a surgical system according to the disclosure to perform a mock surgical procedure on a cadaveric canine surgical specimen 700. A right sacro-iliac luxation (SIL) and a left sacro-iliac fracture (SIF) were created in a Labrador-sized dog. The right SIL was reduced using two reduction handles (or joysticks) 300 respectively anchored in the ipsilateral ischial tuberosity and craniodorsal ridge of the iliac wing. Following fluoroscopic evidence of reduction, the joysticks 300 were rigidly coupled to their respective variable friction 6-axis hydrostatic arms 200, thus securing the hemipelvis in place (FIG. 2). Next, a surgical washer was laid over the gluteal musculature of the surgical specimen 700, then slid on the skin until it was superimposed over the sacral body on fluoroscopic images. From that location, a stab incision was performed straight down to the iliac wing (FIG. 2).

Figure 7:
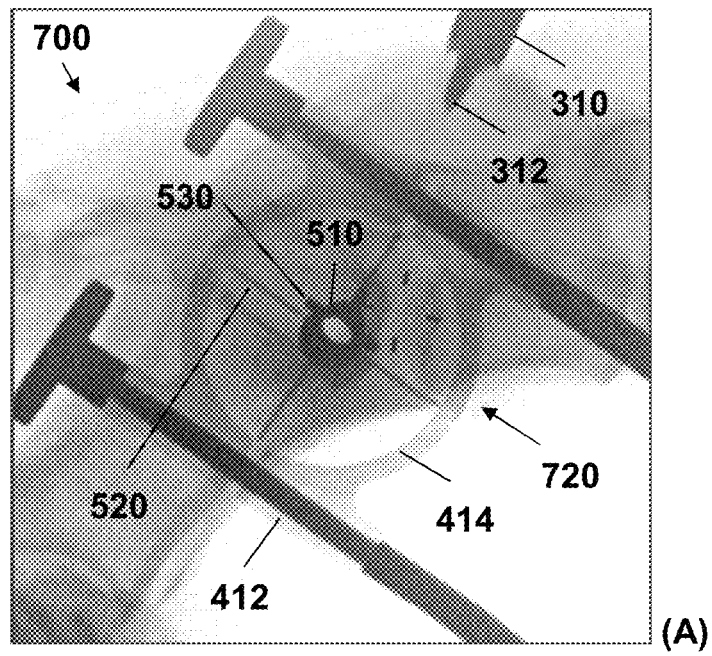
FIG. 7 includes x-ray images for fluoroscopic evaluation of the aiming device during positioning for location and orientation in a surgical specimen. Panel (A) is a top view of the aiming device showing off-axis misalignment of the drill guide sleeve, as well as non-overlapping misalignment of the proximal and distal aiming guides. Panel (B) is a top view of the aiming device as properly positioned and oriented, showing on-axis alignment of the drill guide sleeve, as well as overlapping alignment of the proximal and distal aiming guides.
Figure 7:
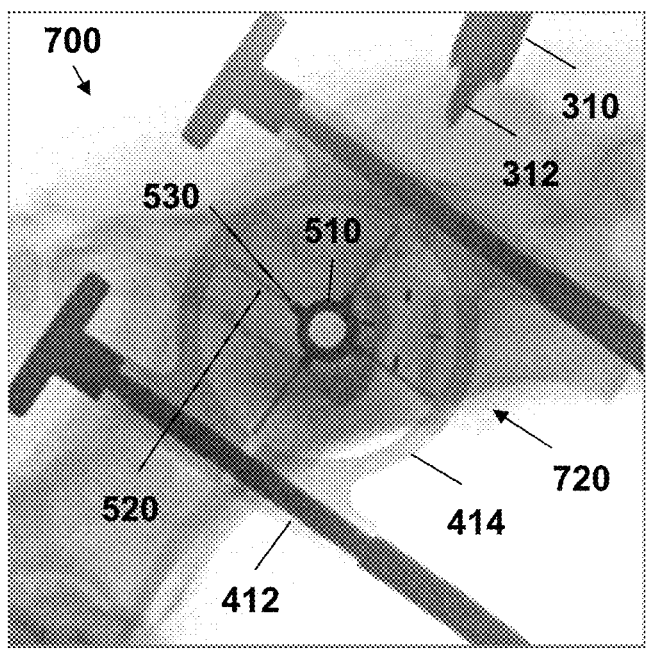

The aiming device 500 was then inserted into the wound and loosely coupled to its fixation arm 400. Using the crosshair aiming guides 520 and fin aiming guides 530, the aiming device 500 was easily and promptly manipulated in position. Proper location over the sacral body 720 and orientation perpendicular to the sagittal plane were ascertained using fluoroscopic views (FIG. 7) before locking the fixation arm 400 in place. FIG. 7 (panel (A)) is a top view of the aiming device showing off-axis misalignment of the drill guide sleeve, as well as non-overlapping misalignment of the proximal and distal aiming guides. FIG. 7 (panel (B)) is a top view of the aiming device as properly positioned and oriented, showing on-axis alignment of the drill guide sleeve, as well as overlapping alignment of the proximal and distal aiming guides. It took about 4 minutes to move from a cursory to a final accurate position. This time includes planar and angular corrections as well time for the surgical team to step in and out of the radiation area.

Sequential drilling of the pilot and glide holes was performed through the drill guide and aiming device 500 using appropriately sized reduction sleeves 510. Fixation was achieved using an ilio-sacral aluminum screw. Following lag screw fixation, the joysticks 300 and aiming device 500 were removed, and each stab wound was closed using a single stitch. Screw orientation in the transverse and dorsal panes was evaluated on pane radiographs as well as CT based MPRs. The procedure was repeated on the opposite side. Post-operative lateral and ventro-dorsal radiographs following reduction and fixation of the SIL using the surgical system 10 and aiming device 500 showed the central location of the lag screw and its orientation nearly perpendicular to the sagittal plane. As importantly, the entire shaft of the screw was located within the safe sacral corridor. Post-operative radiographs following reduction and fixation of the SIF using the surgical system 10 and aiming device 500 similarly showed showing proper placement of both lag screws in the sacral safe corridor. Thus, the aiming device 500 was effective in providing fast and accurate orientation of fixation screws in MIO of SIL/F.

Example 3: Surgical System and Drill Guide/Aiming Device

Example 3 and corresponding FIGS. 1-9 illustrate a surgical system 10 and related components, including a drill guide/aiming device 500, according to the disclosure and as generally described above in Examples 1 and 2. Example 3 provides further detail regarding the surgical system 10 and related components, as well as their use to perform Minimally invasive osteosynthesis (MIO) of sacroiliac luxation/fractures (SIL/F) in a cadaveric canine surgical specimen.

Surgical System and Components:

The surgical system 10 includes main components: one or two MIO reduction handles 300, two or three table-bound variable friction 6-axis articulated arms 200 (reduction arm) or 400 (fixation arm), and a drill guide/aiming device 500. The articulated arms 200, 400 are used to adjust and then secure the position of the reduction handles 300 and aiming device 500 during reduction and fixation, respectively. The reduction handles 300 includes a self-drilling and self-tapping threaded rod 310 and insertion tip 312 anchored into bone of the surgical subject 700. A cannulated handle or tube 320 is then inserted over the rod 310 and secured in place. The reduction handles 300 allow percutaneous manipulation of bone fragments of the surgical subject 700 (e.g., the hemipelvis for SIF/L) until appropriate reduction or positioning is achieved. After reduction, the reduction handle 300 it attached or mounted to a corresponding table-bound, 6-axis reduction arm 200.

FIG. 3 illustrates a variable-friction, 6-axis arm 200 or 400 that can be used as a reduction arm 200 or a fixation arm 400. The fully articulated arms 200, 400 include a ball-and-socket universal joint (360° rotatable) at each end of a corresponding arm element 210, 410 and a central variable friction hinge fitted with a locking knob or mechanism 220, 420. Each arm 200, 400 (e.g., at proximal ends 200A, 400A thereof) is secured to a surgical table 100 via a dedicated clamp or mounting structure 230, 430. The distal ends 200B, 400B of the arms 200, 400 can be fitted with a reduction handle 300 (i.e., for reduction) or an aiming device 500 (i.e., for fixation), respectively, along with related attachment structures. The rigidity of each arm 200, 400 is precisely controlled via the locking knob 220, 420 that can be loosened to allow smooth and precise positioning of the arm free end, or tightened to lock the arm in any desired resting position. The fixation arm 400 is used to precisely control the location and orientation of the aiming device 500 in space. The variable friction feature of these 6-axis arms 200, 400 allows the surgeon to secure these instruments in their desired and final position, for example based on incremental adjustments and corresponding position/orientation verification (e.g., via radiographic imaging).

The aiming device 500 structure is described in Example 2 above. On intra-operative fluoroscopic images, the crosshair formed by the stainless steel K-wire aiming guides 520 of the upper lucent component 540 act as the reticle/scope or the rear sight of a rifle while the thicker fin aiming guides 530 at the lower end of the sleeve 510 mimic the front sight of the rifle. The position of the crosshair structures in relation to the fin structures allows the surgeon to rapidly assess, and correct, the orientation of the aiming device 500 until its ideal position is achieved (FIG. 7, panel (B) showing alignment with proper position and orientation). The aiming device 500 is linked to the table-bound dedicated variable friction 6-axis fixation arm 400 using a circular tubular clamp, as well as a rail-like sliding handle 412 and quick release coupling clamp. While the central and lower distal portions or sections 500B of the aiming device 500 are inserted in the gluteal musculature of the surgical subject 700, the upper proximal portion or section 500A remains outside the surgical wound and, being radiolucent, allows an unobstructed view of the sacrum throughout surgery.

Surgical Technique:

The surgical system 10 was used to perform reduction and fixation of a sacroiliac luxation and a contralateral sacroiliac luxation-fracture on a canine cadaver, a 12-year-old Labrador retriever who had died of natural. A right SIL and a left SIL/F were created in the surgical specimen 700, and preoperative imaging confirmed the presence of the aforementioned lesions.

Figure 8:
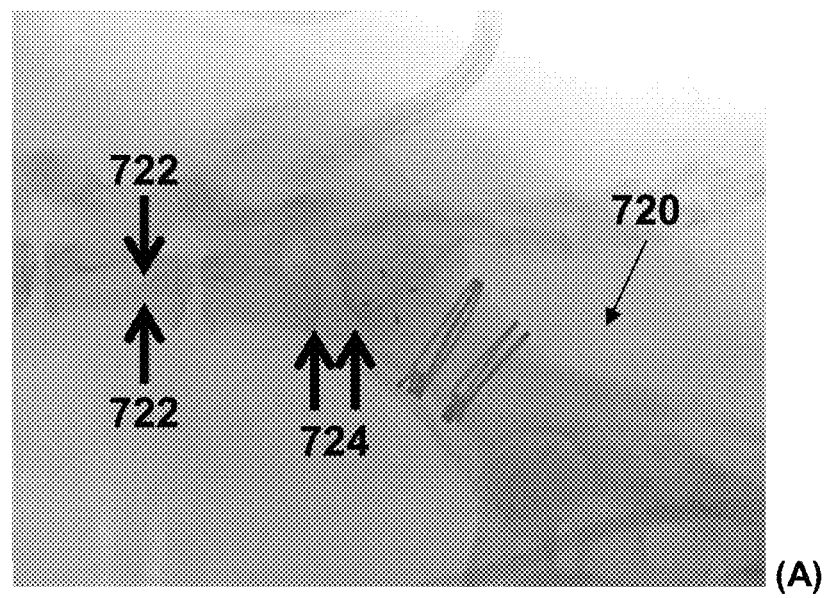
FIG. 8 illustrates the sacral body 720 after proper adjustment and alignment to control roll and yaw and prior to fixation. Panel (A) is an intraoperative fluoroscopic image, and panel (B) is a corresponding CT based 3D reconstruction of the lumbosacral spine after segmentation of the pelvis.
Figure 8:
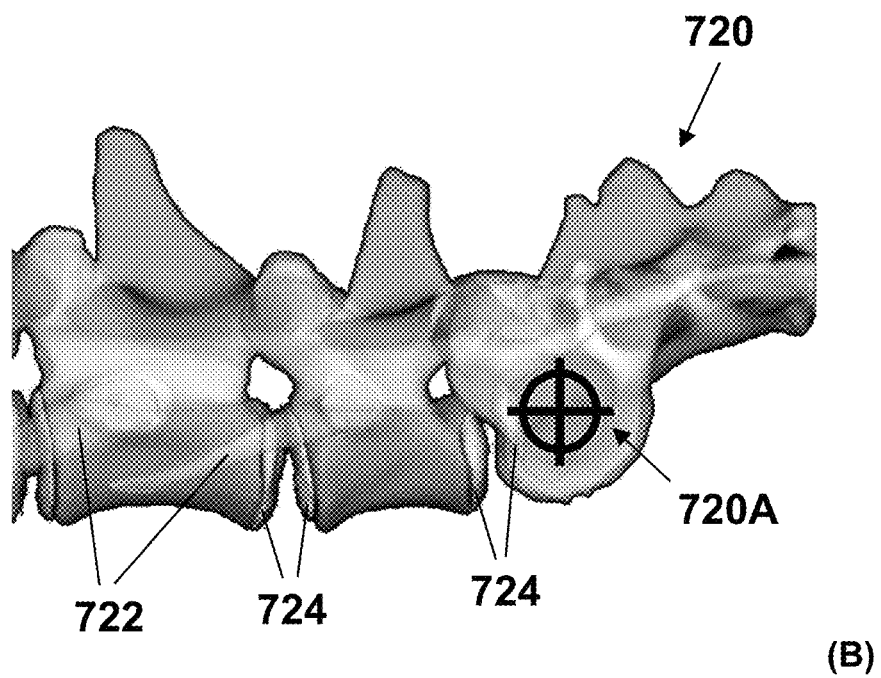

Prior to operation, the patient or surgical specimen 700 was positioned in lateral recumbency over a radiolucent surgical table 100 that allowed multi axial remote motorized adjustments. The image intensifier unit 620 of a C-arm x-ray image acquisition unit 600 (OEC 9900 Elite: General Electric, Salt Lake City, Utah, USA) was placed immediately below the bottom surface 120 of the surgical table 100 and approximately centered underneath the sacrum of the surgical specimen 700. The image emitter unit 610 of the image acquisition unit 600 was situated above the top surface 110 of the surgical table 100 and above the sacrum of the surgical specimen 700. Cursory spinal alignment was visually assessed and altered by means of a conforming vacuum bean bag. Sacral body alignment of the surgical specimen 700 was adjusted under fluoroscopic guidance by axially adjusting the table 100. Accurate sacral position was achieved when dorsoventral superimposition of L7 transverse processes (dorsoventral roll) and parallelism of L7-S1 end plates (craniocaudal yaw) were ascertained. FIG. 8 illustrates proper adjustments of the lumbosacral spine in an actual clinical case. In this position, the transverse axis of the sacral body 720 is perpendicular to the sagittal plane and parallel to the X-ray beam. FIG. 8 illustrates the sacral body 720 after proper adjustment and alignment to control roll and yaw (panel (A): intraoperative fluoroscopic image; panel (B): corresponding CT based 3D reconstruction of the lumbosacral spine after segmentation of the pelvis). As shown, accurate superimposition of L7 processes 722 (roll controlled) and simultaneous parallelism of the L7/S1 end plates 724 (yaw controlled) indicate proper lumbosacral alignment. In that position, the transverse axis 720A of the sacral body 720 is perpendicular to the sagittal plane and the safe sacral corridor is parallel to the X-ray beam. Following fluoroscopic confirmation of accurate patient positioning, routine draping was performed. All operating room personnel wore lead aprons and thyroid shields under a surgical gown, and stood at least three meters away from the X-ray source 610 during fluoroscopic imaging.

A small stab incision was made over right ischial tuberosity prior to placement of the MIO reduction handle 300. A second additional reduction handle 300 may be inserted in the craniodorsal crest of the iliac wing through a small skin incision if desired for additional placement and immobilization control. The hemipelvis was manipulated by the surgeon using the reduction handle 300 to reduce the SIL. Once the surgeon believed reduction had been achieved, the handles 300 were rigidly secured to their respective reduction arms 200 and the reduction arms 200 were locked in position. Reduction of the SIL and sacral orientation were fluoroscopically evaluated after surgical personnel moved away by at least three meters from the x-ray source 610. The procedure of reduction adjustment, arm 200 locking, and fluoroscopically evaluation was repeated until accurate reduction was achieved and confirmed.

With the SIL reduced and stabilized via the reduction arm 200 and handle 300, the location of the sacrum was determined by moving a surgical washer over the surgical subject's skin until its center appeared superimposed with the sacral body 720 on fluoroscopic images. The location was marked with a surgical pen and a stab incision was made through the skin and gluteal musculature to the iliac wing. The incision was then enlarged using straight Metzembaum scissors. Next, the aiming device 500 was positioned over the incision, inserted into the wound and placed into its desired position.

In the aiming device 500, the difference in thickness, as well as the distance between the proximal and distal aiming guides 520, 530 were selected to facilitate identification of the upper and lower components on intraoperative fluoroscopic images. This allowed for fast and accurate reorientation of the aiming device 500 until its central sleeve 510 component appeared as a perfect circle centered over the sacral body, thus guaranteeing perpendicularity to the sagittal plane (FIG. 7, panel (B)). To facilitate incremental adjustments of the aiming device 500 position and orientation, the table-bound fixation arm 400 was kept snug, but not fully locked. Once proper placement and orientation of the aiming device 500 was fluoroscopically verified, the fixation arm 400 was locked in place using the locking mechanism 420. As for reduction, surgical personnel stepped away from the C-arm during acquisition of fluoroscopic images.

Appropriately sized drill sleeves were inserted in the aiming device 500 via the central sleeve or guide portion 510, and matching drill bits were used to respectively create pilot and glide holes through the entire width of the sacral body and iliac wing, respectively. The sacral pilot hole was then tapped before screw insertion. To reduce metal artifact on post-operative imaging, an aluminum screw (4 mm×50 mm) rather than a stainless-steel surgical cortical bone screw was used. The screw was tightened to achieve lag fixation prior to skin closure. This first screw was purposely oriented with a slight caudal deviation from an optimal position to allow for the insertion of a second lag screw for the MIO treatment of the contralateral, left SIL/F. Post-operative radiographs and CT scan of the lumbosacral and pelvic regions were obtained prior to treatment of the left SIL/F using the same surgical technique.

Figure 9:
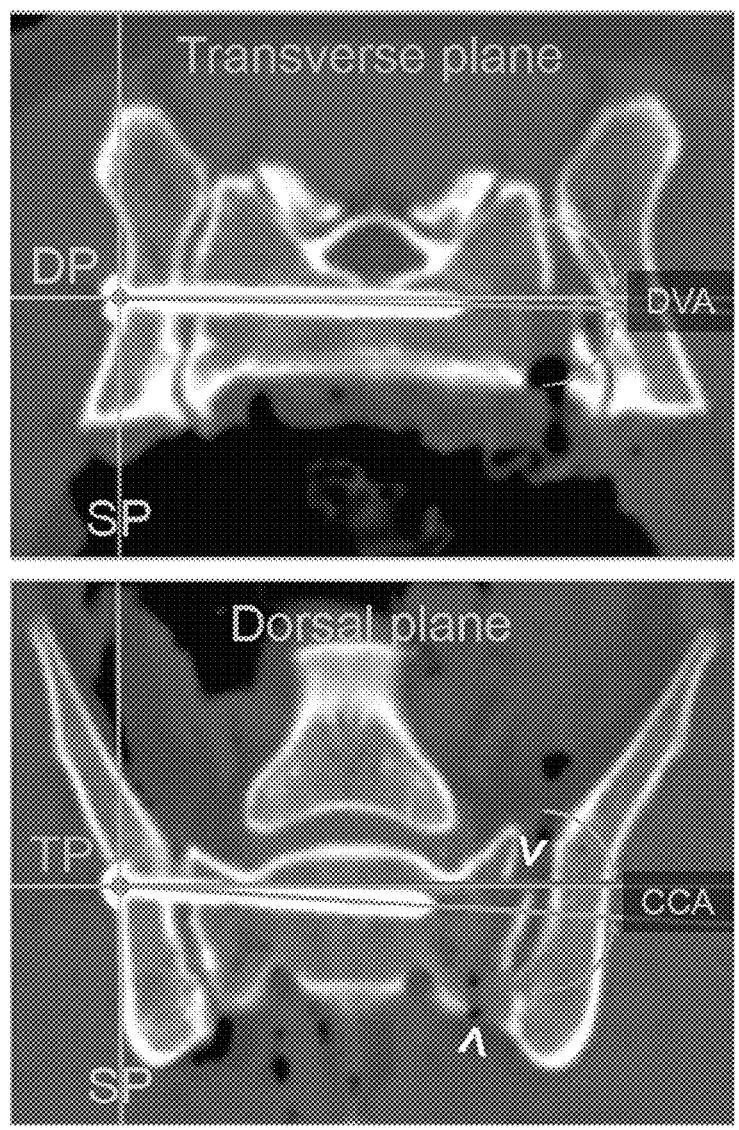
FIG. 9 includes computed tomography (CT) multiplanar reconstruction (MPR) images of transverse plane (top) and dorsal plane (bottom), from which objective measurements of the dorsoventral screw angle, craniocaudal screw angle, and sacral purchase determined. The left SIL/F is indicated by arrow heads, and the first screw (right side) was deliberately angled slightly caudally to allow for the placement of a second screw on the contralateral left side.

Post-Operative Assessment: Objective measurements of screw angles and sacral purchase were made using post-operative CT multiplanar reconstructions to assess dorsoventral screw angle (DVA) and craniocaudal angle (CCA) (FIG. 9). DVA is the angle between the axis of the screw and the dorsal plane. CCA is the angle between the screw and the transverse plane. The DVA and CCA values of both screws were measured in the transverse and dorsal planes, respectively, and were positive for dorsal and cranial screw deviations, respectively. Negative screw angles indicated ventral and caudal screw orientations. The DVA and CCA values were $-1.2°$ and $-3.8°$ respectively for the first (right) screw and $-0.9°$ and $+2.6°$ respectively for the second contralateral left screw. Sacral purchase was 100% within the sacral body for both screws.

Summary: This example illustrates several advantages of the surgical system 10 and its associated components and surgical methods, including: stable maintenance of SIL/F reduction throughout surgery, reliable and accurate screw placement in the sacral body (both insertion position and orientation), and protection of surgical personnel against ionizing radiations from the x-ray image acquisition unit.

Secured/Stable Arms: Securing the reduction handles 300 and aiming device 500 to the arms 200, 400 means that reduction and fixation can be achieved without the arms 200, 400 encroaching in the surgeon's space. Further, stable reduction was maintained throughout the procedure without the need for temporary fixation. Additionally, there was no need for the surgeon to manually hold the reduction aids, which in turn allowed surgical personnel to step away from the X-ray source 610 and patient every time intraoperative fluoroscopic imaging was performed. This is an improvement relative to traditional SIL/F MIO where a surgical assistant must maintain contact with the reduction aids and drill sleeves within the C-arm x-ray imaging unit 600 free space until fixation is achieved, which in turn increases personnel exposure to radiations due to the proximity to the X-ray source.

Accurate Screw Placement: By enabling the surgeon to lock the aiming device 500 in situ, the surgical system 10 can reduce human aiming error associated with current MIO SIL/F techniques. The radiolucent design of the aiming device 500 eases the placement of a contralateral lag screw in cases of bilateral SIL/F. By allowing an unobstructed view of the sacrum throughout surgery, the aiming device 500 enables identification of a contralateral safe implantation corridor while concomitantly accommodating for the presence of a previous lag screw.

Radiation Protection: In the disclosed surgical system 10, the C-arm x-ray imaging unit 600 is placed in a so called "inverted" position, with the image intensifier 620 immediately under the surgical table 100 and therefore in close proximity to the patient. Although this C-arm 600 orientation enhances image resolution and allows wide access to the surgical field, it nearly doubles exposure to primary beam and scattered radiations from the emitter unit 610 above the surgical table 100. Therefore, because of substantial and insidious health hazards, the inverted C-arm position is not recommended when using standard MIO techniques. In the disclosed surgical system 10, however, this drawback becomes irrelevant, because the surgical personnel can step away from the X-ray source 610 to a safe distance when imaging is performed. Thus, the surgical system 10 allows orientation of the imaging unit 600 in a manner that improves image quality without any of the associated health risks from radiation exposure.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the apparatus, compounds, compositions, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

PARTS LIST

10 surgical system
100 work surface or table
110 top surface or side
120 bottom surface or side
200 (first) reduction arm (A: proximal region or end; B: distal region or end)
202 second reduction arm
210 reduction arm elements
220 reduction arm locking mechanism
230 reduction arm mounting structure
300 (first) reduction handle (A: proximal region or end; B: distal region or end)
302 second reduction handle
310 reduction rod
312 insertion pin/threaded tip
314 proximal end/attachment means
320 reduction tube
322 gripping or anchoring teeth
322A rotating washer with gripping teeth
324 knurling
326 compression/locking nut
330 gripping portion
340 reduction sleeve
342 tapered distal tip
344 longitudinal slots
346 stress reduction gaps
348 knurling
400 fixation arm (A: proximal region or end; B: distal region or end)
410 fixation arm elements
412 fixation arm longitudinally extending retaining members
$D_R$ distance between retaining members
414 clamp
420 fixation arm locking mechanism
430 fixation arm mounting structure
500 fixation drill guide/aiming device (A: proximal region or end; B: distal region or end)
510 drill guide sleeve (A: proximal region or end; B: distal region or end)
512 circumferential recess
520 radiopaque proximal (or cis or near) aiming guides
530 radiopaque distal (or trans or far) aiming guides
532 sleeve
540 radiolucent body
542 channels
544 central hole
L length of drill guide sleeve
D interior diameter or width of drill guide sleeve
Z axial longitudinal direction of drill guide sleeve
R radial direction relative to longitudinal axis of drill guide sleeve
Θ angular position
l aiming guide length w at aiming guide width
600 image acquisition unit
610 emitter unit
620 intensifier unit
700 surgical subject or specimen
710 fixation means/screw
720 fixation location/sacral body
720A transverse axis or sacral corridor
722 L7 processes
724 L7/S1 end plates
730 reduction location
x, y, z horizontal, horizontal, and vertical directions

What is claimed is:

1. A surgical system comprising:
a work surface;
a reduction arm mounted to the work surface at a proximal region of the reduction arm, wherein the reduction arm is articulatable relative to the work surface, and the reduction arm is lockable in position relative to the work surface;
a reduction handle mounted to the reduction arm at a distal region of the reduction arm, wherein:
(i) the reduction handle is adapted to attach to a surgical subject, and
(ii) reduction handle comprises (A) a reduction rod comprising an insertion pin at a distal end of the reduction rod, (B) a reduction tube adapted to receive the reduction rod therethrough, and (C) a reduction sleeve slidably mounted to a distal end of the reduction tube, the reduction sleeve being formed from a flexible material and having a tapered distal tip with longitudinal slots permitting expansion of the tapered distal tip;
a fixation arm mounted to the work surface at a proximal region of the fixation arm, wherein the fixation arm is articulatable relative to the work surface, and the fixation arm is lockable in position relative to the work surface;
a fixation drill guide mounted to the fixation arm at a distal region of the fixation arm, wherein the fixation drill guide is adapted to receive a fixation screw therethrough for insertion into the surgical subject; and
an image acquisition unit directed toward the work surface, wherein the image acquisition unit is lockable in position relative to the work surface.

2. The system of claim 1, comprising at least two reduction arms and at least two reduction handles.

3. The system of claim 1, wherein:
the reduction arm comprises at least two reduction arm elements rotatably mounted to each other; and
the fixation arm comprises at least two fixation arm elements rotatably mounted to each other.

4. The system of claim 1, wherein the reduction tube comprises a radiolucent material.

5. A surgical system comprising:
a work surface;
a reduction arm mounted to the work surface at a proximal region of the reduction arm, wherein the reduction arm is articulatable relative to the work surface, and the reduction arm is lockable in position relative to the work surface;
a reduction handle mounted to the reduction arm at a distal region of the reduction arm, wherein the reduction handle is adapted to attach to a surgical subject;
a fixation arm mounted to the work surface at a proximal region of the fixation arm, wherein the fixation arm is articulatable relative to the work surface, and the fixation arm is lockable in position relative to the work surface;
a fixation drill guide mounted to the fixation arm at a distal region of the fixation arm, wherein (i) the fixation drill guide is adapted to receive a fixation screw therethrough for insertion into the surgical subject, and (ii) the fixation drill guide is a minimally invasive lucent aiming device and drill guide comprising:
a drill guide sleeve defining a longitudinal axis therethrough and adapted to receive a fixation screw therethrough for insertion into a surgical subject;
at least two radially extending radiopaque proximal aiming guides positioned at different angular positions and extending outwardly from a proximal end of the drill guide sleeve; and
at least two radially extending radiopaque distal aiming guides positioned at different angular positions and extending outwardly from a distal end of the drill guide sleeve;
wherein the angular position for each proximal aiming guide is the same as the angular position for a corresponding distal aiming guide; and
an image acquisition unit directed toward the work surface, wherein the image acquisition unit is lockable in position relative to the work surface.

6. The system of claim 1, wherein:
the fixation arm comprises two longitudinally extending retaining members at the distal region of the fixation arm and spaced apart by a distance of at least 1 cm; and
the fixation drill guide is mounted to the fixation arm between the two longitudinally extending retaining members.

7. The system of claim 1, wherein the work surface is articulatable.

8. The system of claim 1, wherein the image acquisition unit is an x-ray imaging unit.

9. The system of claim 8, wherein:
the image acquisition unit comprises an emitter unit and an intensifier unit;
the emitter unit is positioned above the work surface; and
the intensifier unit is positioned below the work surface.

10. A minimally invasive lucent aiming device and drill guide comprising:
a drill guide sleeve defining a longitudinal axis therethrough and adapted to receive a fixation screw therethrough for insertion into a surgical subject;
at least two radially extending radiopaque proximal aiming guides positioned at different angular positions and extending outwardly from a proximal end of the drill guide sleeve; and
at least two radially extending radiopaque distal aiming guides positioned at different angular positions and extending outwardly from a distal end of the drill guide sleeve;
wherein the angular position for each proximal aiming guide is the same as the angular position for a corresponding distal aiming guide.

11. The aiming device and drill guide of claim 10, further comprising a radiolucent body enclosing or attached to the proximal aiming guides and positioned at the proximal end of the drill guide sleeve.

12. The aiming device and drill guide of claim 10, wherein each corresponding pair of a proximal aiming guide and a distal aiming guide at the same angular position has relative lengths and widths such that one aiming guide is longer and narrower than the corresponding opposing aiming guide in the corresponding pair.

13. The aiming device and drill guide of claim 12, wherein the proximal aiming guide is longer and narrower than the corresponding distal aiming guide in the corresponding pair.

14. The aiming device and drill guide of claim 10, wherein:
   the proximal aiming guides have lengths in a range from 0.5 cm to 5 cm; and
   the distal aiming guides have lengths in a range from 0.5 mm to 5 mm.

15. The aiming device and drill guide of claim 10, wherein the drill guide sleeve defines an open interior volume having a width in a range from 1 mm to 10 mm.

16. The aiming device and drill guide of claim 10, wherein the drill guide sleeve has a length in a range from 1 cm to 10 cm.

17. The aiming device and drill guide of claim 10, wherein the drill guide sleeve comprises a radiolucent material.

18. The aiming device and drill guide of claim 10, comprising:
   four radiopaque proximal aiming guides at angular positions of 0°, 90°, 180°, and 270°; and
   four corresponding radiopaque distal aiming guides at corresponding angular positions of 0°, 90°, 180°, and 270°.

* * * * *